United States Patent
Takeda

(10) Patent No.: US 10,966,591 B2
(45) Date of Patent: Apr. 6, 2021

(54) MEDICAL SIGNAL PROCESSING DEVICE, MEDICAL DISPLAY DEVICE, AND MEDICAL OBSERVATION SYSTEM INVOLVING APPENDING COLOR GAMUT IDENTIFICATION INFORMATION TO THE PICTURE SIGNAL RESULTING FROM CONVERSION

(71) Applicant: Sony Olympus Medical Solutions Inc., Tokyo (JP)

(72) Inventor: Takayuki Takeda, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 15/746,917

(22) PCT Filed: Jun. 23, 2016

(86) PCT No.: PCT/JP2016/068729
§ 371 (c)(1),
(2) Date: Jan. 23, 2018

(87) PCT Pub. No.: WO2017/022358
PCT Pub. Date: Feb. 9, 2017

(65) Prior Publication Data
US 2019/0133417 A1    May 9, 2019

(30) Foreign Application Priority Data
Aug. 6, 2015    (JP) .............................. JP2015-156427

(51) Int. Cl.
*A61B 1/00*    (2006.01)
*H04N 7/18*    (2006.01)
(Continued)

(52) U.S. Cl.
CPC ...... *A61B 1/00009* (2013.01); *A61B 1/00045* (2013.01); *A61B 1/04* (2013.01);
(Continued)

(58) Field of Classification Search
CPC ............ A61B 1/00009; A61B 1/00045; A61B 1/00114; A61B 1/0669; A61B 1/042;
(Continued)

(56) References Cited

U.S. PATENT DOCUMENTS

2007/0124645 A1*  5/2007  Ito ....................... H04L 63/0428
                                                            714/758
2009/0027490 A1*  1/2009  Hirai ....................... A61B 1/04
                                                            348/65
(Continued)

FOREIGN PATENT DOCUMENTS

JP         3734104 B2     10/2005
JP         2009-521840 A   6/2009
(Continued)

OTHER PUBLICATIONS

ST 2068:2013—SMPTE Standard—Stereoscopic 3D Frame Compatible Packing and Signaling for HDTV, Jul. 29 2013, SMPTE (Year: 2013).*

(Continued)

*Primary Examiner* — Francis Geroleo
(74) *Attorney, Agent, or Firm* — Xsensus LLP

(57) ABSTRACT

A medical signal processing device 6 receives a picture signal imaged by a medical observation device 2 and processes the picture signal. The medical signal processing device 6 includes: a signal input unit 61 that receives the picture signal; a first signal converting unit 62 that converts the picture signal received by the signal input unit 61 from an RGB signal into a luminance signal and a color difference signal by performing a matrix calculating process; an iden- (Continued)

tification information appending unit 63 that appends color gamut identification information related to a color gamut of the picture signal and corresponding to the matrix calculating process, to the picture signal resulting from the conversion; and a signal output unit 64 that outputs the picture signal to which the color gamut identification information has been appended, to either a medical display device 4 or a medical recording device provided externally.

14 Claims, 13 Drawing Sheets

(51) Int. Cl.
| | |
|---|---|
| *A61B 1/04* | (2006.01) |
| *H04N 1/64* | (2006.01) |
| *G09G 5/02* | (2006.01) |
| *H04N 1/60* | (2006.01) |
| *H04N 13/15* | (2018.01) |
| *H04N 13/139* | (2018.01) |
| *A61B 1/06* | (2006.01) |

(52) U.S. Cl.
CPC ............. *G09G 5/02* (2013.01); *H04N 1/6058* (2013.01); *H04N 1/646* (2013.01); *H04N 7/18* (2013.01); *H04N 13/139* (2018.05); *H04N 13/15* (2018.05); *A61B 1/00114* (2013.01); *A61B 1/00117* (2013.01); *A61B 1/042* (2013.01); *A61B 1/0669* (2013.01); *G09G 2340/06* (2013.01); *G09G 2370/04* (2013.01); *H04N 7/183* (2013.01)

(58) Field of Classification Search
CPC .. A61B 1/00117; H04N 13/15; H04N 13/139; H04N 7/183
See application file for complete search history.

(56) References Cited

U.S. PATENT DOCUMENTS

| | | | |
|---|---|---|---|
| 2009/0284554 A1 | 11/2009 | Doser | |
| 2010/0128114 A1* | 5/2010 | Cheung | A61B 1/00059 348/65 |
| 2010/0271465 A1* | 10/2010 | Lee | H04N 21/234327 348/51 |
| 2011/0128438 A1 | 6/2011 | Yamashita et al. | |
| 2012/0033041 A1* | 2/2012 | Nagaraj | H04N 21/234327 348/43 |
| 2012/0044324 A1* | 2/2012 | Lee | H04N 13/178 348/43 |
| 2013/0314516 A1* | 11/2013 | Uchihara | H04N 5/3675 348/65 |
| 2015/0085074 A1* | 3/2015 | Kudo | A61B 1/00009 348/45 |
| 2015/0272422 A1* | 10/2015 | Aoyama | A61B 1/00006 348/68 |
| 2015/0294463 A1* | 10/2015 | Takahashi | G02B 23/2423 348/71 |
| 2016/0261846 A1* | 9/2016 | Kasumi | H04N 7/18 |
| 2017/0048561 A1* | 2/2017 | Oh | H04N 21/23 |

FOREIGN PATENT DOCUMENTS

| | | |
|---|---|---|
| JP | 2013-244250 A | 12/2013 |
| WO | 2010/023884 A1 | 3/2010 |

OTHER PUBLICATIONS

International Search Report dated Sep. 13, 2016 in PCT/JP2016/068729 filed Jun. 23, 2016.
Notification of the First Office Action dated Jul. 2, 2019, issued in corresponding Chinese Patent Application No. 2016800448369, 15 pages (with English translation).
Extended European Search Report dated Jul. 17, 2019, issued in corresponding European Patent Application No. 16832637.9, 6 pages.

* cited by examiner

FIG.4

| No. | ITEMS | VALUES(w/o Parity) |
|---|---|---|
| 0 | ADF | 000h |
| 1 | | 3FFh |
| 2 | | 3FFh |
| 3 | DID | 055h |
| 4 | SDID | 005h |
| 5 | DC | 001h |
| 6 | UDW | 004h:ITU-R BT.709<br>005h:ITU-R BT.2020<br>006h:Native |
| 7 | CS | Check Sum |

FIG.11

| User Data Words | | User Data Word bits | | | | | | | | |
|---|---|---|---|---|---|---|---|---|---|---|
| UDW | Function | b9 | b8 | b7 | b6 | b5 | b4 | b3 | b2 | b1 | b0 |
| 1 | FC UDW1 | $\overline{b8}$ | P | fpa3 | fpa2 | fpa1 | fpa0 | QSF | FPS | sv1 | sv0 |
| 2 | GRID Position | $\overline{b8}$ | P | f1y1 | f1y0 | f1x1 | f1x0 | f0y1 | f0y0 | f0x1 | f0x0 |
| 3 | FC UDW3 | $\overline{b8}$ | P | sf1 | sf0 | ci1 | ci0 | 0 | SP | CFR | FV |

FIG.12

| SYSTEM CATEGORY | SYSTEM NAME | LUMINANCE OR R'G'B' SAMPLE NUMBER PER EFFECTIVE LINE | NUMBER OF EFFECTIVE LINES PER FRAME | FRAMERATE (Hz) |
|---|---|---|---|---|
| UHDTV1 | 3840×2160/23.98/P | 3840 | 2160 | 24/1.001 |
| | 3840×2160/24/P | 3840 | 2160 | 24 |
| | 3840×2160/25/P | 3840 | 2160 | 25 |
| | 3840×2160/29.97/P | 3840 | 2160 | 30/1.001 |
| | 3840×2160/30/P | 3840 | 2160 | 30 |
| | 3840×2160/50/P | 3840 | 2160 | 50 |
| | 3840×2160/59.94/P | 3840 | 2160 | 60/1.001 |
| | 3840×2160/60/P | 3840 | 2160 | 60 |
| | 3840×2160/120/P | 3840 | 2160 | 120 |
| UHDTV2 | 7680×4320/23.98/P | 7680 | 4320 | 24/1.001 |
| | 7680×4320/24/P | 7680 | 4320 | 24 |
| | 7680×4320/25/P | 7680 | 4320 | 25 |
| | 7680×4320/29.97/P | 7680 | 4320 | 30/1.001 |
| | 7680×4320/30/P | 7680 | 4320 | 30 |
| | 7680×4320/50/P | 7680 | 4320 | 50 |
| | 7680×4320/59.94/P | 7680 | 4320 | 60/1.001 |
| | 7680×4320/60/P | 7680 | 4320 | 60 |
| | 7680×4320/120/P | 7680 | 4320 | 120 |

Background Art

FIG.13

| PARAMETER | | UHDTV (ITU-R BT.2020) | | HDTV (ITU-R BT.709) | |
|---|---|---|---|---|---|
| PICTURE ASPECT RATIO | | 16:9 | | 16:9 | |
| NUMBER OF PIXELS (HORIZONTAL × VERTICAL) | | 7,680×4,320, 3840×2,160 | | 1,920×1,080 | |
| FRAME FREQUENCY (Hz) | | 120, 60, 60/1.001, 50, 30, 30/1.001, 25, 24, 24/1.001 | | 60, 60/1.001, 50, 30, 30/1.001, 25, 24, 24/1.001 | |
| SCANNING | | PROGRESSIVE SCANNING | | PROGRESSIVE SCANNING, INTERLACED SCANNING | |
| COLORIMETRIC SYSTEM (CIE 1931) | | x | y | x | y |
| | R | 0.708 | 0.292 | 0.640 | 0.330 |
| | G | 0.170 | 0.797 | 0.300 | 0.600 |
| | B | 0.131 | 0.046 | 0.150 | 0.060 |
| | WHITE | D65 | | D65 | |
| | | 0.3127 | 0.3290 | 0.3127 | 0.3290 |
| NON-LINEAR TRANSFER FUNCTION | | $E' = \begin{cases} 4.5E, & 0 \le E < \beta \\ \alpha E^{0.45} - (\alpha-1), & \beta \le E \le 1 \end{cases}$ $\alpha = 1.099$ and $\beta = 0.018$ (10-BIT SYSTEM) $\alpha = 1.0993$ and $\beta = 0.0181$ (12-BIT SYSTEM) | | $E' = \begin{cases} 4.5E, & 0 \le E < 0.018 \\ 1.099E^{0.45} - 0.099, & 0.018 \le E \le 1 \end{cases}$ | |
| LUMINANCE SIGNAL | | $Y'_C = (0.2627R + 0.6780G + 0.0593B)'$ | $Y' = 0.2627R' + 0.6780G' + 0.0593B'$ | $Y' = 0.2126R' + 0.7152G' + 0.0722B'$ | |
| COLOR DIFFERENCE SIGNAL | | $C'_{BC} = \begin{cases} \frac{B'-Y'_C}{1.9404}, & B'-Y'_C \le 0 \\ \frac{B'-Y'_C}{1.5816}, & 0 < B'-Y'_C \end{cases}$ $C'_{RC} = \begin{cases} \frac{R'-Y'_C}{1.7184}, & R'-Y'_C \le 0 \\ \frac{R'-Y'_C}{0.9936}, & 0 < R'-Y'_C \end{cases}$ | $C'_B = \frac{B'-Y'}{1.8814}$ $C'_R = \frac{R'-Y'}{1.4746}$ | $C'_B = \frac{B'-Y'}{1.8556}$ $C'_R = \frac{R'-Y'}{1.5748}$ | |
| PIXEL STRUCTURE OF LUMINANCE AND COLOR DIFFERENCE SIGNALS | | 4:4:4, 4:2:2, 4:2:0 | | 4:2:2 | |
| QUANTIZATION BIT NUMBER | | 10 BITS OR 12 BITS | | 8 BITS OR 10 BITS | |
| QUANTIZATION METHOD | | $R', G', B', Y' : D' = INT[(219 \times E' + 16) \times 2^{n-8}]$ $C'_B, C'_R : D' = INT[(224 \times E' + 128) \times 2^{n-8}]$ (n:BIT NUMBER) | | SAME AS SHOWN ON LEFT | |

Background Art

MEDICAL SIGNAL PROCESSING DEVICE, MEDICAL DISPLAY DEVICE, AND MEDICAL OBSERVATION SYSTEM INVOLVING APPENDING COLOR GAMUT IDENTIFICATION INFORMATION TO THE PICTURE SIGNAL RESULTING FROM CONVERSION

TECHNICAL FIELD

The present invention relates to a medical signal processing device that receives an input of a picture signal corresponding to a result of a medical examination performed on the inside of an examined subject and processes the picture signal, a medical display device that displays an image based on a picture signal processed by the medical signal processing device, and a medical observation system including the medical signal processing device and the medical display device.

BACKGROUND ART

Conventionally, in medical fields, a medical observation system is known in which the inside of an examined subject such as a human being (the inside of a living body) is imaged so as to observe the inside of the living body (see Patent Literature 1, for example).

The medical observation system (an electronic endoscope device) described in Patent Literature 1 includes: a medical observation device (an endoscope) that images the inside of the living body and outputs a picture signal; a medical signal processing device (a processor device) that receives an input of the picture signal from the medical observation device, converts (hereinafter, "YC conversion") the picture signal from an RGB signal into a luminance signal and a color difference signal (a Y, $C_B/C_R$ signal) and outputs the result of the conversion; and a medical display device (a monitor) that generates a display-purpose picture signal (an RGB signal) by converting (hereinafter, "RGB conversion") the picture signal (the Y, $C_B/C_R$ signal) received as an input from the medical signal processing device from the Y, $C_B/C_R$ signal into an RGB signal and further displays an image based on the picture signal (the RGB signal).

FIG. 12 is a table illustrating picture signals having a 4K resolution level and an 8K resolution level that are standardized by an international organization. FIG. 13 is a table illustrating picture parameters of picture signals having a High Definition (HD) level, a 4K resolution level, and an 8K resolution level that are standardized by an international organization. In the following description, the 4K resolution level and the 8K resolution level will simply be referred to as "4K" and "8K", respectively.

In FIG. 12, "Ultra-High Definition Television (UHDTV) 1" corresponds to a 4K picture signal, whereas "UHDTV2" corresponds to an 8K picture signal. Further, in FIG. 13, "UHDTV" corresponds to 4K and 8K picture signals, whereas "High Definition Television (HDTV)" corresponds to an HD picture signal.

Incidentally, in recent years, medical observation devices configured to output high-resolution picture signals of either 4K or 8K have been developed. Further, as illustrated in FIGS. 12 and 13, transfer schemes used with such high-resolution picture signals are standardized by international organizations (e.g., Society of Motion Picture and Television Engineers (SMPTE) and International Telecommunication Union (ITU)).

Further, as illustrated in FIG. 13, for HD picture signals (see "HDTV" in FIG. 13), a standard defines that a calculation formula (see the items corresponding to "luminance signal" and "color difference signal" in FIG. 12) compliant with ITU-R BT.709 is to be used for a matrix calculating process in the YC conversion. Further, for 4K and 8K picture signals (see "UHDTV" in FIG. 13), a standard defines that a calculation formula (see the items corresponding to "luminance signal" and "color difference signal" in FIG. 13) compliant with ITU-R BT.2020 is to be used for a matrix calculating process in the YC conversion.

In this situation, although omitted from FIG. 13, the international organization defines that, for a 4K picture signal, it is also acceptable to use not only the calculation formula compliant with ITU-R BT.2020, but also the calculation formula compliant with ITU-R BT.709, for the matrix calculating process in the YC conversion.

CITATION LIST

Patent Literature

Patent Literature 1: Japanese Laid-open Patent Publication No. 2013-244250

DISCLOSURE OF INVENTION

Technical Problem

As explained above, to perform the matrix calculating process in the YC conversion on a 4K picture signal, it is acceptable to use either of the two calculation formulae, namely, the calculation formula compliant with ITU-R BT.2020 and the calculation formula compliant with ITU-R BT.709. Accordingly, for example, let us discuss a situation where the medical signal processing device described in Patent Literature 1 performs the YC conversion on a 4K picture signal by performing a matrix calculating process while using the calculation formula compliant with ITU-R BT.2020.

In this situation, even when being able to recognize that the picture signal input thereto from the medical display processing device is a 4K picture signal, the medical display device described in Patent Literature 1 is not able to find out whether the medical signal processing device used the calculation formula compliant with ITU-R BT.2020 or the calculation formula compliant with ITU-R BT.709, during the YC conversion. Further, for example, when the medical display device performs an RGB conversion (to convert from the Y, $C_B/C_R$ signal into an RGB signal) on the picture signal (the Y, $C_B/C_R$ signal) input thereto from the medical signal processing device while using the calculation formula compliant with ITU-R BT.709 instead of ITU-R BT.2020 used by the medical signal processing device and further displays an image based on the picture signal (the RGB signal) resulting from the RGB conversion, it turns out that the medical display device displays the image while using a color gamut (ITU-R BT.709) different from the color gamut (ITU-R BT.2020) of the picture signal processed by the medical signal processing device. In other words, a problem arises where it is not possible to display an image having excellent color reproducibility.

To cope with this situation, there is a demand for a technique that makes it possible to display an image having excellent color reproducibility while using an appropriate color gamut.

In view of the circumstances described above, it is an object of the present invention to provide a medical signal processing device, a medical display device, and a medical observation system that make it possible to display an image having excellent color reproducibility while using an appropriate color gamut.

Solution to Problem

To solve the above-described problem and achieve the object, a medical signal processing device according to the present invention receives a picture signal imaged by a medical observation device and processes the picture signal, and includes: a signal input unit that receives the picture signal; a first signal converting unit that converts the picture signal received by the signal input unit from an RGB signal into a luminance signal and a color difference signal by performing a matrix calculating process; an identification information appending unit that appends color gamut identification information related to a color gamut of the picture signal and corresponding to the matrix calculating process, to the picture signal resulting from the conversion; and a signal output unit that outputs the picture signal to which the color gamut identification information has been appended, to either an external medical display device or an external medical recording device.

Moreover, in the above-described medical signal processing device according to the present invention, the picture signal imaged by the medical observation device is a picture signal having a 4K resolution level.

Moreover, in the above-described medical signal processing device according to the present invention, the first signal converting unit converts the picture signal received by the signal input unit by performing either the matrix calculating process compliant with ITU-R BT.709 or the matrix calculating process compliant with ITU-R BT.2020, when the first signal converting unit performed the conversion by performing the matrix calculating process compliant with ITU-R BT.709, the identification information appending unit appends the color gamut identification information indicating ITU-R BT.709 to the picture signal resulting from the conversion, and when the first signal converting unit performed the conversion by performing the matrix calculating process compliant with ITU-R BT.2020, the identification information appending unit appends the color gamut identification information indicating ITU-R BT.2020 to the picture signal resulting from the conversion.

Moreover, in the above-described medical signal processing device according to the present invention, the first signal converting unit converts the picture signal received by the signal input unit from the RGB signal into the luminance signal and the color difference signal by performing the matrix calculating process and converts the picture signal resulting from the conversion into serial data defined by a predetermined SDI format, and the identification information appending unit appends the color gamut identification information by using a section of use that is usable by a user and is in a data identification word defined by the predetermined SDI format.

Moreover, in the above-described medical signal processing device according to the present invention, the first signal converting unit converts the picture signal received by the signal input unit from the RGB signal into the luminance signal and the color difference signal by performing the matrix calculating process and converts the picture signal resulting from the conversion into serial data defined by a predetermined SDI format, and the identification information appending unit appends the color gamut identification information to an ancillary data multiplex enabled region that is in the serial data and is defined by the predetermined SDI format.

Moreover, in the above-described medical signal processing device according to the present invention, the first signal converting unit converts the picture signal received by the signal input unit from the RGB signal into the luminance signal and the color difference signal by performing the matrix calculating process and also converts the picture signal resulting from the conversion into serial data defined by a predetermined SDI format, and the identification information appending unit appends the color gamut identification information only to a Y data sequence from between the Y data sequence and a $C_B/C_R$ data sequence in the serial data.

Moreover, in the above-described medical signal processing device according to the present invention, the signal input unit receives two picture signals including a left-eye picture signal and a right-eye picture signal, the first signal converting unit converts the left-eye picture signal and the right-eye picture signal received by the signal input unit each from the RGB signal into the luminance signal and the color difference signal by performing the matrix calculating process and generates a 3D picture signal from the left-eye picture signal and the right-eye picture signal resulting from the conversion, to the 3D picture signal, the identification information appending unit appends the color gamut identification information and appends scheme identification information related to a 3D transfer scheme of the 3D picture signal, and the signal output unit outputs the 3D picture signal to which the color gamut identification information and the scheme identification information have been appended, to either the medical display device or the medical recording device.

Moreover, in the above-described medical signal processing device according to the present invention, the 3D transfer scheme is a line by line scheme.

Moreover, in the above-described medical signal processing device according to the present invention, the identification information appending unit uses a 3DFC ancillary data packet defined by SMPTE ST 2068 as the scheme identification information.

Moreover, in the above-described medical signal processing device according to the present invention, the identification information appending unit uses an undefined section of use of a payload in the 3DFC ancillary data packet, as the scheme identification information.

Moreover, a medical display device according to the present invention receives a picture signal processed by an external medical signal processing device and displays an image based on the picture signal, wherein the picture signal has appended thereto color gamut identification information related to a color gamut of the picture signal and corresponding to a matrix calculating process performed when the medical signal processing device converted the picture signal from an RGB signal into a luminance signal and a color difference signal, and the medical display device includes: a second signal converting unit that generates a display-purpose picture signal by converting the picture signal from the luminance signal and the color difference signal into the RGB signal in accordance with the matrix calculating process, based on the color gamut identification information appended to the picture signal; and a display unit that displays an image based on the display-purpose picture signal.

Moreover, in the medical display device according to the present invention, the picture signal is a 3D picture signal generated based on a left-eye picture signal and a right-eye picture signal, the 3D picture signal includes the color gamut identification information appended thereto and includes scheme identification information related to a 3D transfer scheme of the 3D picture signal appended thereto, and the second signal converting unit generates the display-purpose picture signal, by converting the 3D picture signal from the luminance signal and the color difference signal into the RGB signal in accordance with the matrix calculating process, based on the color gamut identification information appended to the 3D picture signal, and performing a signal processing process corresponding to the 3D transfer scheme of the 3D picture signal, based on the scheme identification information appended to the 3D picture signal.

Moreover, a medical observation system according to the present invention includes: a medical observation device that images an inside of an examined subject and supplies a picture signal obtained by the imaging; a medical signal processing device that receives the picture signal and processes the picture signal; and a medical display device that displays an image based on the picture signal processed by the medical signal processing device, wherein the medical signal processing device includes: a signal input unit that receives the picture signal; a first signal converting unit that converts the picture signal received by the signal input unit from an RGB signal into a luminance signal and a color difference signal by performing a matrix calculating process; an identification information appending unit that appends color gamut identification information related to a color gamut of the picture signal and corresponding to the matrix calculating process, to the picture signal resulting from the conversion; and a signal output unit that outputs the picture signal to which the color gamut identification information has been appended, to the medical display device, and the medical display device includes: a second signal converting unit that generates a display-purpose picture signal by converting the picture signal from the luminance signal and the color difference signal into the RGB signal in accordance with the matrix calculating process, based on the color gamut identification information appended to the picture signal; and a display unit that displays an image based on the display-purpose picture signal.

Moreover, in the above-described medical observation system according to the present invention, the medical observation device is an endoscope.

Advantageous Effects of Invention

The medical signal processing device according to at least one aspect of the present invention is configured to receive an input of a picture signal corresponding to a result of an medical examination performed on the inside of an examined subject and to convert (the YC conversion) the picture signal from an RGB signal into a Y, $C_B/C_R$ signal. Further, the medical signal processing device is configured to append the color gamut identification information related to the color gamut of the picture signal and corresponding to the matrix calculating process in the YC conversion, to the picture signal resulting from the YC conversion and to further output the information-appended picture signal to either a medical display device or a medical recording device provided externally.

Accordingly, when the picture signal including the color gamut identification information is directly output to the medical display device, the medical display device is able to recognize what calculation formula was used in the YC conversion performed by the medical signal processing device, by assessing the color gamut identification information. Consequently, as a result of the medical display device generating the display-purpose picture signal by converting (the RGB conversion) the picture signal (the Y, $C_B/C_R$ signal) input thereto from the medical signal processing device from the $C_B/C_R$ signal into the RGB signal in accordance with the calculation formula and further displaying the image based on the display-purpose picture signal (the RGB signal), it is possible to display an image having excellent color reproducibility while using an appropriate color gamut.

Further, when the picture signal including the color gamut identification information is output to the medical recording device, as a result of the medical recording device recording the picture signal therein and further outputting the picture signal together with the color gamut identification information to the medical display device, it is possible to display, by performing the process described above, an image having excellent color reproducibility while using an appropriate color gamut.

The medical display device according to at least one aspect of the present invention is configured to receive an input of a picture signal processed by a medical signal processing device. Further, based on color gamut identification information appended to the picture signal, the medical display device is configured to convert (the RGB conversion) the picture signal (the Y, $C_B/C_R$ signal) from the Y, $C_B/C_R$ signal into an RGB signal in accordance with the calculation formula used by the medical signal processing device and is further configured to display an image based on the picture signal (the RGB signal) resulting from the RGB conversion.

In other words, by assessing the color gamut identification information, the medical display device is able to recognize what calculation formula was used in the YC conversion performed by the medical signal processing device. Accordingly, as a result of the medical display device generating the display-purpose picture signal, by performing the RGB conversion corresponding to the calculation formula on the picture signal (the Y, $C_B/C_R$ signal) input thereto from the medical signal processing device and further displaying an image based on the display-purpose picture signal (the RGB signal), it is possible to display an image having excellent color reproducibility while using an appropriate color gamut.

Because the medical observation system according to at least one aspect of the present invention includes the medical signal processing device and the medical display device described above, the medical observation system is able to achieve the same advantageous effects as those achieved by the medical signal processing device and the medical display device.

BRIEF DESCRIPTION OF DRAWINGS

FIG. 4 is a table illustrating an example of color gamut identification information (a UID) appended by the identification information appending unit illustrated in FIG. 2.

FIG. 11 is a table illustrating payloads defined by SMPTE ST 2068.

FIG. 12 is a table illustrating picture signals having a 4K resolution level and an 8K resolution level that are standardized by an international organization.

FIG. 13 is a table illustrating picture parameters of picture signals having a High Definition (HD) level, a 4K resolution level, and an 8K resolution level that are standardized by an international organization.

BEST MODE FOR CARRYING OUT THE INVENTION

Figure 1:
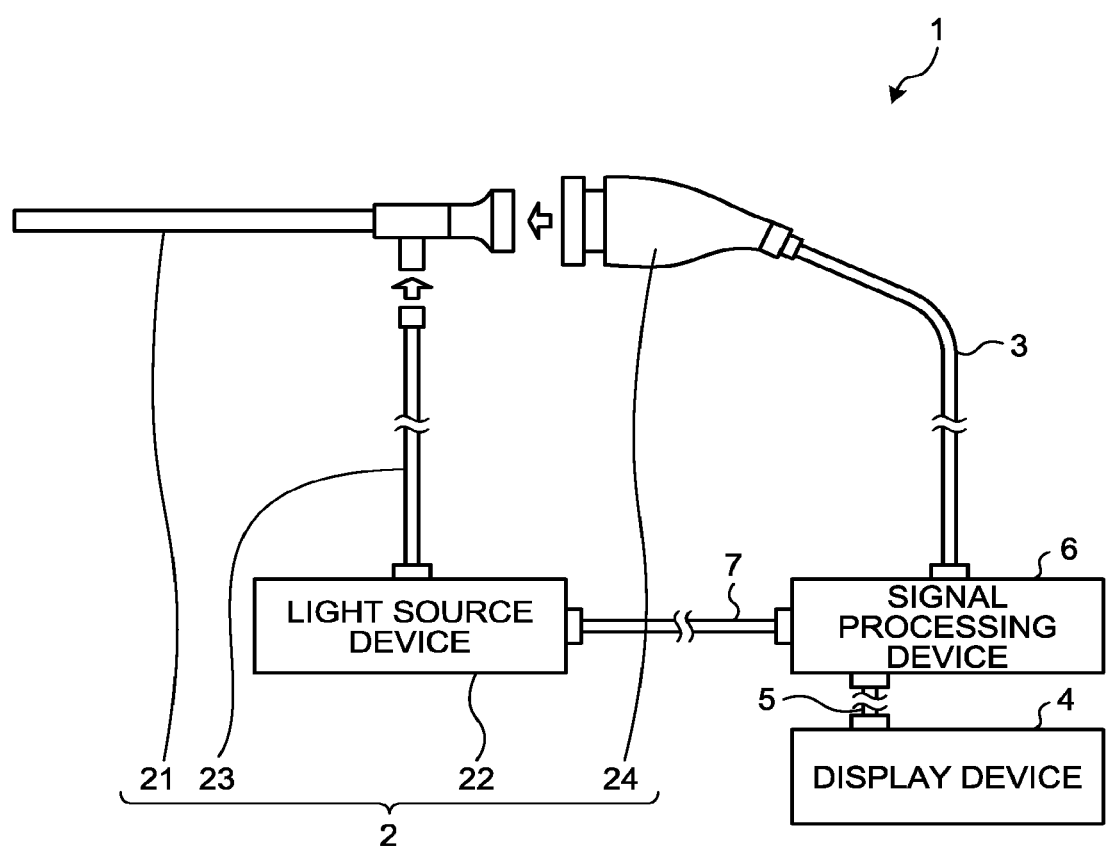
FIG. 1 is a drawing illustrating a schematic configuration of a medical observation system according to a first embodiment of the present invention.

Embodiments to carry out the present invention (hereinafter, "embodiments") will be explained below with reference to the drawings. The present invention is not limited by the embodiments described below. Further, in the drawings, mutually the same parts are referred to by using the same reference characters.

First Embodiment

A Schematic Configuration of a Medical Observation System

FIG. 1 is a drawing illustrating a schematic configuration of a medical observation system 1 according to a first embodiment of the present invention.

The medical observation system 1 is a system used in medical fields and used for observing the inside of an examined subject such as a human being (the inside of a living body). As illustrated in FIG. 1, the medical observation system 1 includes an endoscope 2, a first transfer cable 3, a display device 4, a second transfer cable 5, a signal processing device 6, and a third transfer cable 7.

The endoscope 2 has functions as a medical observation device according to the present invention and is configured to examine the inside of the living body and to output a signal corresponding to a result of the medical examination. As illustrated in FIG. 1, the endoscope 2 includes an insertion part 21, a light source device 22, a light guide 23, and a camera head 24.

The insertion part 21 is rigid, has an oblong shape, and is configured to be inserted into the living body. Provided on the inside of the insertion part 21 is an optical system structured with one or more lenses and configured to converge light to form an image of the subject.

The light source device 22 has one end of the light guide 23 connected thereto and is configured to supply the one end of the light guide 23 with light used for illuminating the inside of the living body, under control of the signal processing device 6.

The one end of the light guide 23 is detachably connected to the light source device 22, whereas the other end of the light guide 23 is detachably connected to the insertion part 21. Further, the light guide 23 is configured to transfer the light supplied by the light source device 22 from the one end to the other end thereof, so as to supply the insertion part 21 with the light. The light supplied to the insertion part 21 is emitted from the tip end of the insertion part 21 and is radiated onto the inside of the living body. The light radiated onto the inside of the living body (the image of the subject) is converged by the optical system provided in the insertion part 21.

The camera head 24 is detachably connected to the basal end of the insertion part 21. Further, under the control of the signal processing device 6, the camera head 24 is configured to take the image of the subject converged by the insertion part 21 and to output an imaged signal (hereinafter, "raw signal") resulting from the imaging process. The raw signal corresponds to the "picture signal corresponding to a result of a medical examination" of the present invention.

In the first embodiment, the camera head 24 is configured to perform a photoelectric conversion to convert the raw signal into an optical signal so as to output the raw signal as the optical signal. Further, in the first embodiment, the raw signal is a 4K picture signal. In this situation, the 4K picture signal denotes a picture signal having a resolution of either 4096×2160 or 3840×2160, for example.

One end of the first transfer cable 3 is detachably connected to the signal processing device 6, whereas the other end of the first transfer cable 3 is detachably connected to the camera head 24. More specifically, the first transfer cable 3 is a cable in which a plurality of electric wires (not illustrated) and optical fibers (not illustrated) are provided on the inside of an outer coating, which is the outermost layer.

The plurality of electric wires mentioned above are electric wires used for transferring a control signal output from the signal processing device 6, a timing signal, electric power, and the like to the camera head 24.

The optical fibers mentioned above are optical fibers used for transferring the raw signal (the optical signal) output from the camera head 24 to the signal processing device 6. In this situation, if the raw signal were output from the camera head 24 as an electrical signal, the optical fibers might be replaced with electric wires.

The display device 4 has functions as a medical display device of the present invention. Further, the display device 4 is configured to display an image based on the picture signal processed by the signal processing device 6.

A detailed configuration of the display device 4 will be explained later.

One end of the second transfer cable 5 is detachably connected to the display device 4, whereas the other end of the second transfer cable 5 is detachably connected to the signal processing device 6. Further, the second transfer cable 5 is configured to transfer the picture signal processed by the signal processing device 6 to the display device 4.

In the first embodiment, the second transfer cable 5 is configured by using a transfer cable compliant with a transfer standard of a predetermined Serial Digital Interface (SDI) scheme (e.g., HD-SDI, 3G-SDI, or the like).

The signal processing device 6 has functions as a medical signal processing device of the present invention. Further, the signal processing device 6 is configured so as to include a Central Processing Unit (CPU) and the like and is configured to control operations of the light source device 22, the camera head 24, and the display device 4 in an integrated manner.

A detailed configuration of the signal processing device 6 will be explained later.

One end of the third transfer cable 7 is detachably connected to the light source device 22, whereas the other end of the third transfer cable 7 is detachably connected to the signal processing device 6. Further, the third transfer cable 7 is configured to transfer the control signal from the signal processing device 6 to the light source device 22.

A Configuration of the Signal Processing Device

Next, a configuration of the signal processing device 6 will be explained.

In the following sections, as a function of the signal processing device 6, the explanation will primarily focus on the function of performing a YC conversion (to convert an RGB signal into a Y, $C_B/C_R$ signal) on the raw signal input thereto from the camera head 24 via the first transfer cable 3 and further, converting the result into SDI data streams (corresponding to the serial data of the present invention) defined by a format of a predetermined SDI scheme (e.g., HD-SDI, 3G-SDI, or the like).

Figure 2:
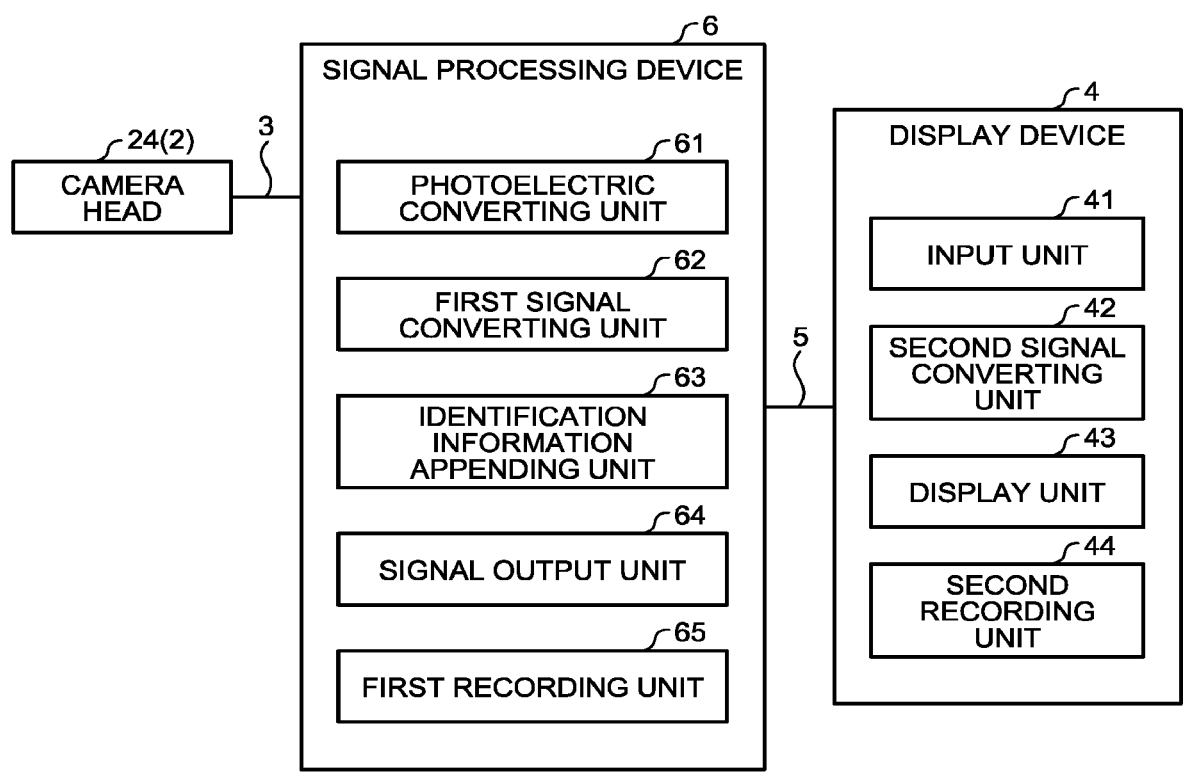
FIG. 2 is a block diagram illustrating a configuration of the signal processing device illustrated in FIG. 1.

FIG. 2 is a block diagram illustrating a configuration of the signal processing device 6.

As illustrated in FIG. 2, the signal processing device 6 includes a photoelectric converting unit 61, a first signal converting unit 62, an identification information appending unit 63, a signal output unit 64, and a first recording unit 65.

The photoelectric converting unit 61 has functions as a signal input unit of the present invention and is configured to receive an input of the raw signal (the optical signal) from the camera head 24 via the first transfer cable 3. Further, the photoelectric converting unit 61 is configured to perform a photoelectric conversion to convert the raw signal (the optical signal) into an electrical signal.

The first signal converting unit 62 is configured to perform a YC conversion (to convert the RGB signal into a Y, $C_B/C_R$ signal) on the raw signal resulting from the photoelectric conversion performed by the photoelectric converting unit 61, by performing either a matrix calculating process compliant with ITU-R BT.709 (a calculation formula defined by the items corresponding to "luminance signal" and "color difference signal" for "HDTV" in FIG. 13) or a matrix calculating process compliant with ITU-R BT.2020 (a calculation formula defined by the items corresponding to "luminance signal" and "color difference signal" for "UHDTV" in FIG. 13).

As explained above, to perform the matrix calculating process in the YC conversion on a 4K picture signal, it is acceptable to use either of the two calculation formulae, namely, the calculation formula compliant with ITU-R BT.709 and the calculation formula compliant with ITU-R BT.2020. In the first embodiment, it is assumed that the first signal converting unit 62 performs the YC conversion on the raw signal (the 4K picture signal) resulting from the photoelectric conversion performed by the photoelectric converting unit 61, by using the matrix calculating process compliant with ITU-R BT.2020.

Further, the first signal converting unit 62 is configured to convert the picture signal (the Y, $C_B/C_R$ signal) resulting from the YC conversion into SDI data streams (a Y data sequence and a $C_B/C_R$ data sequence) corresponding to multiple channels (e.g., four channels) defined by a format of a predetermined SDI scheme (e.g., Level A of 3G-SDI) by performing a publicly-known mapping process.

Figure 3A:
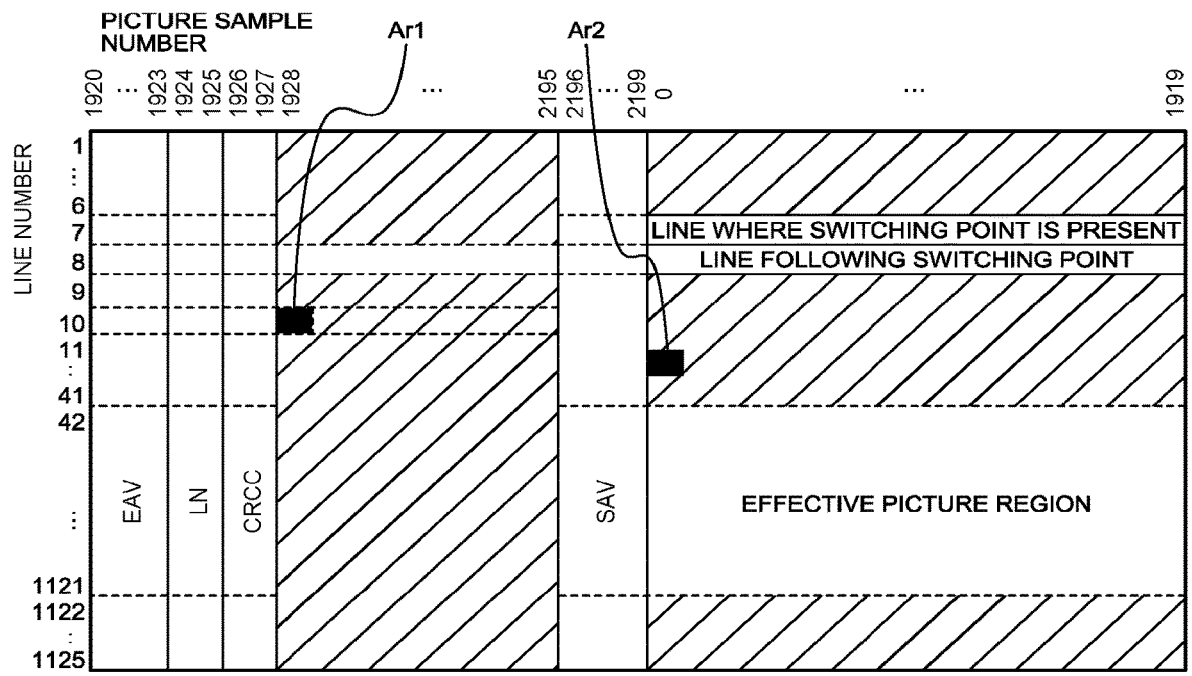
FIG. 3A is a drawing illustrating an example of an SDI data stream (a Y data sequence) resulting from a conversion performed by the first signal converting unit illustrated in FIG. 2.
Figure 3B:
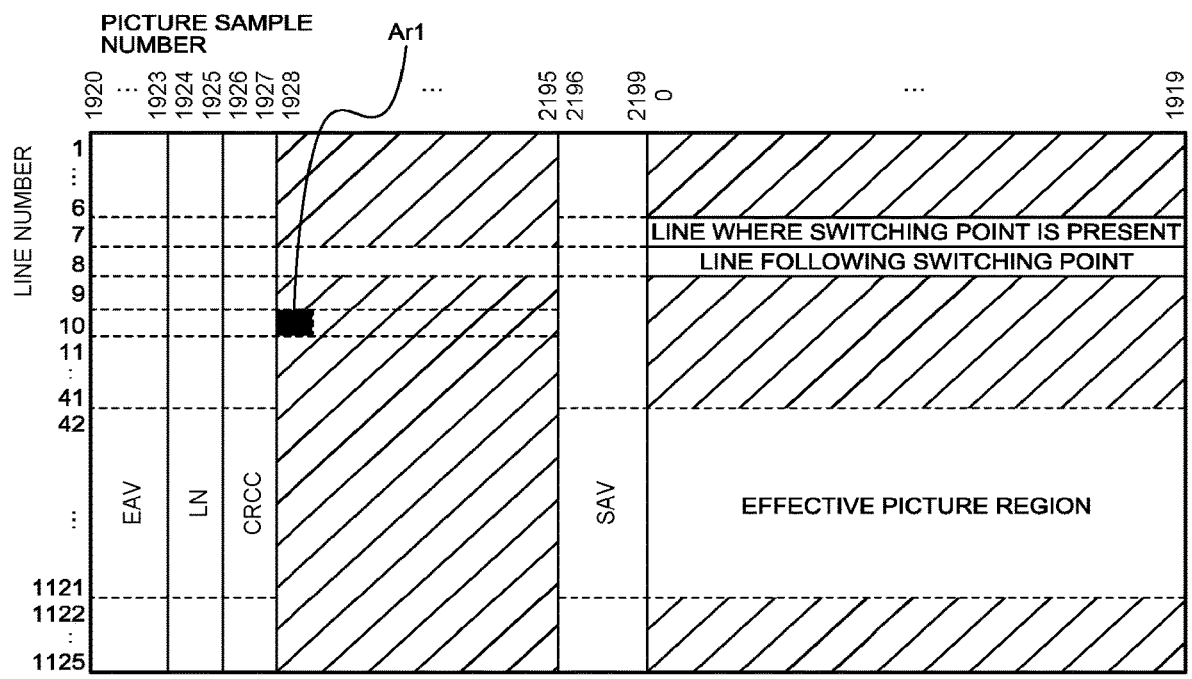
FIG. 3B is a drawing illustrating an example of another SDI data stream (a $C_B/C_R$ data sequence) resulting from the conversion performed by the first signal converting unit illustrated in FIG. 2.

FIG. 3A is a drawing illustrating an example of an SDI data stream (the Y data sequence) resulting from the conversion performed by the first signal converting unit 62. FIG. 3B is a drawing illustrating an example of another SDI data stream (the $C_B/C_R$ data sequence) resulting from the conversion performed by the first signal converting unit 62.

FIGS. 3A and 3B illustrate the SDI data streams (SDI data streams at 1125/P (Level A)) defined by the "Standard for Bit-serial Digital Interface for 1125/60 HDTV Systems (BTA S-004C)" set forth by Association of Radio Industries and Businesses (ARIB).

As illustrated in FIGS. 3A and 3B, for example, the SDI data streams (the Y data sequence and the $C_B/C_R$ data sequence) resulting from the conversion performed by the first signal converting unit 62 are structured in such a manner that a timing reference code called an End of Active Video (EAV) is assigned to picture sample numbers "1920" to "1923"; line number data (LN) is assigned to picture sample numbers "1924" to "1925", error detection code data called a cyclic redundancy check code (CRCC) is assigned to picture sample numbers "1926" to "1927"; and a timing reference code called a Start of Active Video (SAV) is assigned to picture sample numbers "2196" to "2199"; and picture data (a Y, $C_B/C_R$ signal) in an effective picture region is assigned to line numbers "42" to "1121" of picture sample numbers "0" to "1919".

In the present example, in the SDI data streams (the Y data sequence and the $C_B/C_R$ data sequence), the region (indicated with diagonal hatching in FIGS. 3A and 3B) corresponding to picture sample numbers "1928" to "2195" except for line number "8" (the line following a switching point) is a horizontal ancillary data region (HANC). Further, in the SDI data streams (the Y data sequence and the $C_B/C_R$ data sequence), the region (indicated with diagonal hatching in FIGS. 3A and 3B) corresponding to picture sample numbers "0" to "1919" except for line numbers "7" (the line where the switching point is present), "8", and "42" to "1121" is a vertical ancillary data region (VANC).

Further, the horizontal ancillary data region (HANC) and the vertical ancillary data region (VANC) indicated with the diagonal hatching in FIGS. 3A and 3B are ancillary data multiplex enabled regions onto which it is possible to multiplex (add) various types of data.

For example, in the horizontal ancillary data region (HANC), to the region (indicated with solid black as a first region Ar1 in FIGS. 3A and 3B) corresponding to picture sample numbers "1928" to "1938" in line number "10", a payload ID (PID) used for identifying the specifics of the content (e.g., identifying, for example, the picture signal as one of an HD picture signal, a 4K picture signal, and an 8K picture signal) is appended.

The identification information appending unit 63 is configured to append color gamut identification information related to the color gamut of the picture signal and corresponding to the matrix calculating process in the YC conversion performed by the first signal converting unit 62, to the SDI data streams resulting from the conversion performed by the first signal converting unit 62.

In the first embodiment, the identification information appending unit 63 appends the color gamut identification information by using a user IDs (a UID) defined by a predetermined SDI format. From between the Y data sequence and the $C_B/C_R$ data sequence in the SDI data streams, the identification information appending unit 63 appends the color gamut identification information (the UID) only to the Y data sequence. In the vertical ancillary data region (VAMC) of the SDI data stream (the Y data sequence), the identification information appending unit 63 appends the color gamut identification information (the UID) to the region (indicated with solid black as a second region Ar2 in FIG. 3A) corresponding to picture sample numbers "0" to "7" in line number "12". Further, the identification information appending unit 63 appends the color gamut identification information (the UID) to the SDI data stream (only the Y data sequence) corresponding to all the channels (e.g., the four channels) resulting from the conversion performed by the first signal converting unit 62.

FIG. 4 is a table illustrating an example of the color gamut identification information (the UID) appended by the identification information appending unit 63.

As illustrated in FIG. 4, The color gamut identification information (the UID) appended by the identification information appending unit 63 is, for example, compliant with an ancillary data packet structure (the second type) defined in the "Ancillary Data Packet and Space Formatting of Bit-serial Digital Interface for 1125/60 HDTV Systems (BTA S-005)" set forth by Association of Radio Industries and Businesses (ARIB). In other words, the color gamut identification information (the UID) is structured with an ancillary data flag (ADF), a data identification word (DID), a secondary data identification word (SDID), a data count word (DC), a user data word (UDW), and a checksum word (CS).

The ancillary data flag (ADF) is configured with three consecutive words, namely, "000h", "3FFh", and "3FFh" and indicates the start of the color gamut identification information (the UID).

The data identification word (DID) and the secondary data identification word (SDID) are each configured with one word and indicate the type of the user data word (UDW). In the first embodiment, the DID and the SDID indicate that the UID is color gamut identification information used for identifying the color gamut.

According to BTA S-005, for the data identification word (DID), the values (data identification numbers) from "50h" to "5Fh" are in a section of use that is usable for the user; and for the second identification word (SDID), the values (data identification numbers) from "01h" to "FFh" are in a section of use that is usable for the user. In the first embodiment, the values "55h" and "05h" (in the sections of use that are usable for the user) are used as the data identification word (DID) and the secondary data identification word (SDID), respectively, as indicated in FIG. 4. In other words, the identification information appending unit 63 appends the color gamut identification information by using the sections of use that are usable for the user in the data identification words (DID and SDID) defined by the predetermined SDI format.

The data count word (DC) is configured with one word and indicates the number of words of the user data word (UDW).

The user data word (UDW) is configured with one word and indicates the calculation formula used in the matrix calculating process in the YC conversion performed by the first signal converting unit 62.

For example, as illustrated in FIG. 4, when the matrix calculating process is compliant with ITU-R BT.709 (when the display device 4 is caused to display an image by using a color gamut defined by ITU-R BT.709), the user data word (UDW) is set to the value "004h". In contrast, when the matrix calculating process is compliant with ITU-R BT.2020 (when the display device 4 is caused to display an image by using a color gamut defined by ITU-R BT.2020), the user data word (UDW) is set to the value "005h". Further, in consideration that the color gamut may be larger in the future, when the matrix calculating process is compliant with a standard having a larger color gamut than the color gamut defined by ITU-R BT.2020 (when the display device 4 is caused to display an image by using a color gamut defined by such a standard), the user data word (UDW) is set to the value "006h".

In the first embodiment, as explained above, the first signal converting unit 62 performs the YC conversion by performing the matrix calculating process compliant with ITU-R BT.2020. Accordingly, the user data word (UDW) is set to the value "005h".

The checksum word (CS) indicates a checksum value of the UID.

Via the second transfer cable 5, the signal output unit 64 is configured to output the SDI data streams (the Y data sequence and the $C_B/C_R$ data sequence) having the color gamut identification information (the UID) appended thereto and corresponding to the multiple channels (e.g., the four channels), to the display device 4.

The first recording unit 65 is configured to record therein data and the like required by various types of processes performed by the first signal converting unit 62 and the identification information appending unit 63.

Further, the abovementioned signal processing device 6 operates as described below.

Figure 5:
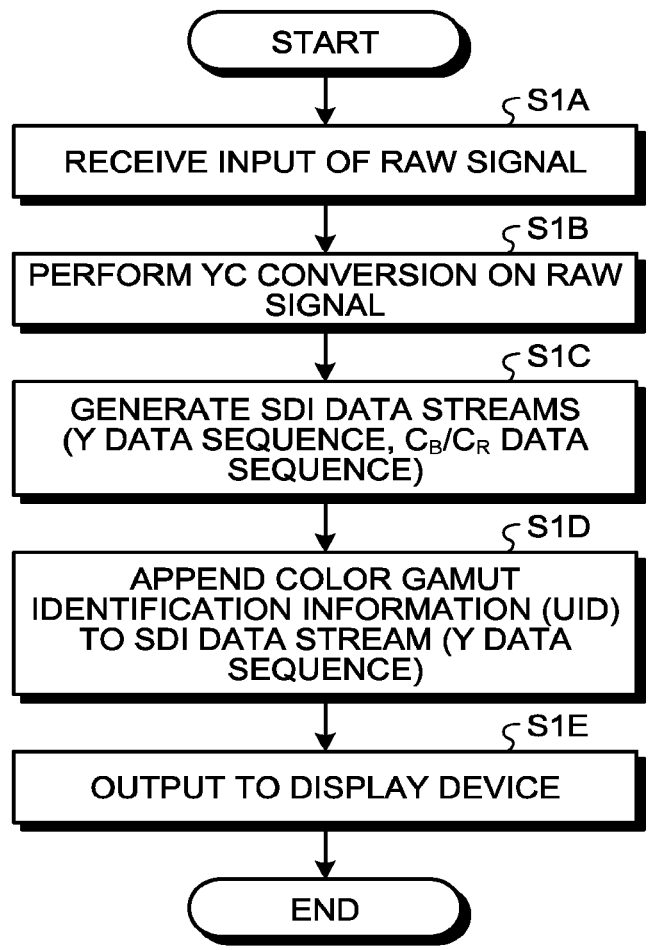
FIG. 5 is a flowchart illustrating an operation (a signal processing method) implemented by the signal processing device illustrated in FIGS. 1 and 2.

FIG. 5 is a flowchart illustrating an operation (a signal processing method) implemented by the signal processing device 6.

First, the photoelectric converting unit 61 receives an input of a raw signal (an optical signal) from the camera head 24 via the first transfer cable 3 (step S1A). Further, the photoelectric converting unit 61 performs a photoelectric conversion to convert the raw signal (the optical signal) into an electrical signal and outputs the raw signal resulting from the photoelectric conversion to the first signal converting unit 62.

Subsequently, the first signal converting unit 62 performs a YC conversion (to convert an RGB signal into a Y, $C_B/C_R$ signal) on the raw signal (a 4K picture signal) resulting from the photoelectric conversion performed by the photoelectric converting unit 61, by performing a matrix calculating process compliant with ITU-R BT.2020 (step S1B).

After that, by performing a mapping process, the first signal converting unit 62 converts the picture signal (the Y, $C_B/C_R$ signal) resulting from the YC conversion into SDI data streams (the Y data sequence and the $C_B/C_R$ data sequence) corresponding to multiple channels (e.g., four channels) (step S1C).

Subsequently, the identification information appending unit 63 appends the color gamut identification information (the UID (in which the user data word [UDW] is set to the value "005h")) only to the Y data sequence in the SDI data streams corresponding to all the channels (e.g., the four channels) (step S1D).

Further, the signal output unit 64 outputs the SDI data streams (the Y data sequence and the $C_B/C_R$ data sequence) having the color gamut identification information (the UID) appended thereto and corresponding to the multiple channels (e.g., the four channels), to the display device 4, via the second transfer cable 5 (step S1E).

A Configuration of the Display Device

Next, a configuration of the display device 4 will be explained.

In the following sections, as a function of the display device 4, the explanation will primarily focus on the function of generating a display-purpose picture signal (an RGB signal) from the SDI data streams corresponding to the multiple channels and having been input thereto from the signal processing device 6 via the second transfer cable 5 and further displaying an image based on the display-purpose picture signal (the RGB signal).

As illustrated in FIG. 2, the display device 4 includes an input unit 41, a second signal converting unit 42, a display unit 43, and a second recording unit 44.

The input unit 41 is configured to receive an input of the SDI data streams (the Y data sequence and the $C_B/C_R$ data sequence) corresponding to the multiple channels (e.g., the four channels) from the signal processing device 6 via the second transfer cable 5.

Based on the BID appended to the first region Ar1 (FIGS. 3A and 3B) in the horizontal ancillary data region (HANG) of the SDI data streams, the second signal converting unit 42 is configured to assess the specifics of the content (e.g., determines which picture signal selected from among an HD picture signal, a 4K picture signal, and an 8K picture signal corresponds to the picture signal, or the like). After that, in accordance with the specifics of the content, the second signal converting unit 42 is configured to convert the SDI data streams into the picture signal (the Y, $C_B/C_R$ signal) observed prior to the conversion into the SDI data streams performed by the first signal converting unit 62, by performing a process opposite of the mapping process performed by the first signal converting unit 62.

Further, based on the color gamut identification information (the UID) appended to the second region Ar2 (FIG. 3A) in the vertical ancillary data region (VANC) of the SDI data streams, the second signal converting unit 42 is configured to learn the calculation formula used in the matrix calculating process in the YC conversion performed by the first signal converting unit 62. After that, the second signal converting unit 42 is configured to generate a display purpose picture signal (an RGB signal) (restores the original picture signal (the RGB signal)) by performing an RGB conversion (to convert the Y, $C_B/C_R$ signal into the RGB signal) corresponding to the matrix calculating process, on the abovementioned picture signal (the Y, $C_D/C_R$ signal) resulting from the conversion.

In other words, when the calculation formula compliant with ITU-R BT.709 was used in the YC conversion performed by the first signal converting unit 62, the second signal converting unit 42 performs a matrix calculating process (an RGB conversion) compliant with ITU-R BT.709, which is the same scheme. In contrast, when the calculation formula compliant with ITU-R BT.2020 was used in the YC conversion performed by the first signal converting unit 62, the second signal converting unit 42 performs a matrix calculating process (an RGB conversion) compliant with ITU-R BT.2020, which is the same scheme.

In the first embodiment, as explained above, the first signal converting unit 62 performed the YC conversion by performing the matrix calculating process compliant with ITU-R BT.2020. For this reason, the second signal converting unit 42 generates the display-purpose picture signal (the RGB signal) having a larger color gamut compliant with ITU-R BT.2020, by learning the calculation formula used in the matrix calculating process based on the color gamut identification information (the UID) and further performing the matrix calculating process (the RGB conversion) compliant with ITU-R BT.2020.

The display unit 43 is configured to display an image based on the display-purpose picture signal (the RGB signal) generated by the second signal converting unit 42.

The second recording unit 44 is configured to record therein data and the like required by various types of processes performed by the second signal converting unit 42.

Further, the abovementioned display device 4 operates as described below.

Figure 6:
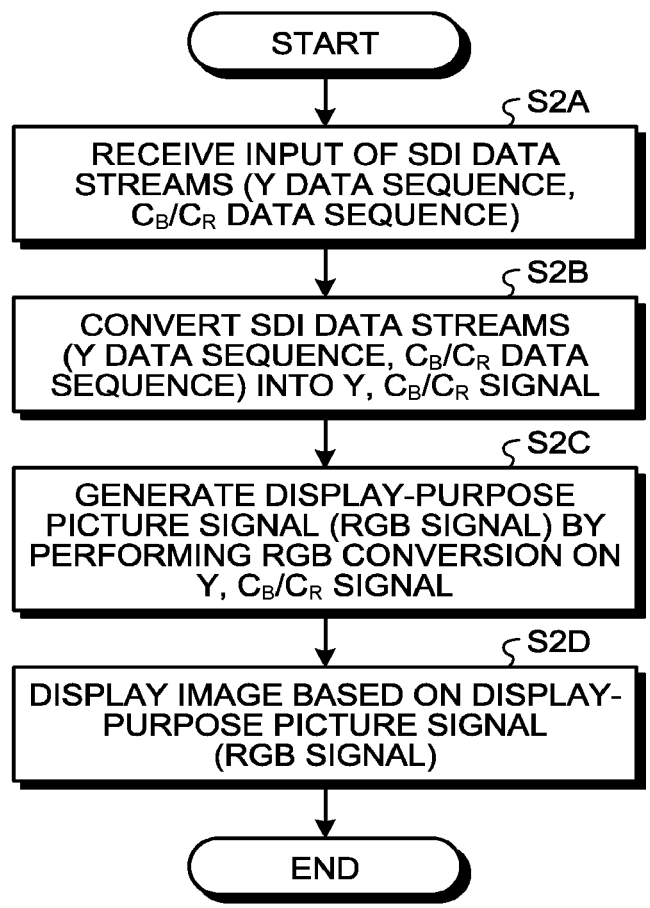
FIG. 6 is a flowchart illustrating an operation (a display method) implemented by the display device illustrated in FIGS. 1 and 2.

FIG. 6 is a flowchart illustrating an operation (a display method) implemented by the display device 4.

First, the input unit 41 receives an input of the SDI data streams (the Y data sequence and the $C_B/C_R$ data sequence) corresponding to the multiple channels (e.g., the four channels) from the signal processing device 6 via the second transfer cable 5 (step S2A).

Subsequently, the second signal converting unit 42 assesses the specifics of the content based on the PID included in the SDI data streams. Further, in accordance with the specifics of the content, the second signal converting unit 42 converts the SDI data streams into the picture signal (the Y, $C_B/C_R$ signal) observed prior to the conversion into the SDI data streams performed by the first signal converting unit 62, by performing a process opposite of the mapping process performed by the first signal converting unit 62 (step S2B).

Subsequently, based on the color gamut identification information (the UID) included in the SDI data streams, the second signal converting unit 42 learns the calculation formula (compliant with ITU-R BT.2020) that was used in the matrix calculating process in the YC conversion performed by the first signal converting unit 62. Further, the second signal converting unit 42 generates a display-purpose 4K picture signal (an RGB signal) by performing a matrix calculating process (an RGB conversion) compliant with ITU-R BT.2020 on the picture signal (the Y, $C_B/C_R$ signal) resulting from the conversion at step S2B (step S2C).

After that, the display unit 43 displays an image (an image having a larger color gamut compliant with ITU-R BT.2020) based on the display-purpose 4K picture signal (the RGB signal) generated at step S2C (step S2D).

The signal processing device 6 according to the first embodiment described above is configured to receive the input of the picture signal corresponding to the result of the medical examination performed on the inside of the living body and to perform the YC conversion on the picture signal. After that, the signal processing device 6 is configured to append the color gamut identification information (the UID) related to the color gamut of the picture signal and corresponding to the matrix calculating process in the YC conversion, to the picture signal (the SDI data streams)

resulting from the YC conversion and to further output the UID-appended picture signal to the external display device 4.

With these arrangements, by assessing the color gamut identification information (the UID) appended to the picture signal (the SDI data streams) input thereto from the signal processing device 6, the display device 4 according to the first embodiment is able to recognize what calculation formula was used in the YC conversion performed by the signal processing device 6. Accordingly, the display device 4 generates the display-purpose picture signal (the RGB signal) by performing the RGB conversion corresponding to the calculation formula on the picture signal (the Y, $C_B/C_R$ signal) input thereto from the signal processing device 6 and further displays the image based on the display-purpose picture signal (the RGB signal). It is therefore possible to display an image having excellent color reproducibility while using an appropriate color gamut.

In particular, because it is impossible to directly view the inside of living bodies in actuality, the user such as a medical doctor who uses the medical observation system 1 is unable to judge, even while looking at the image displayed on the display device 4, whether or not the image is displayed by using an appropriate color gamut. Further, for example, even when the display device is provided with a switch so as to enable the user to change the color gamut of the displayed image with an operation on the switch, the user such as a medical doctor is unable to judge which color gamut is appropriate, even when the color gamut of the image is changed by the operation on the switch, because it is impossible, in actuality, to directly view the inside of living bodies as mentioned above.

In contrast, the display device 4 according to the first embodiment is able to automatically determine the color gamut of the picture signal processed by the signal processing device 6 and to appropriately display the image while using the color gamut. Consequently, the user such as a medical doctor is able to trust the image and to properly perform a diagnosing process.

As explained above, to perform the matrix calculating process in the YC conversion on a 4K picture signal, the international organization defines that it is acceptable to use either of the two calculation formulae, namely, the calculation formula compliant with ITU-R BT.2020 and the calculation formula compliant with ITU-R BT.709. For this reason, according to conventional configurations (where no color gamut identification information (the UID) such as that described in the first embodiment is used), even when the medical display device is able to recognize that the specifics of the content corresponds to a 4K picture signal based on the PID included in the picture signal (the SDI data streams), the display medical display device is not able to find out whether the medical signal processing device used, during the YC conversion, the calculation formulae compliant with ITU-R BT.2020 or the calculation formulae compliant with ITU-R BT.709. Consequently, when the raw signal output from the camera head 24 is a 4K picture signal, it is possible to properly realize the aforementioned advantageous effect (where it is possible to display an image having excellent color reproducibility while using an appropriate color gamut) by using the color gamut identification information (the UID) as described in the first embodiment.

Further, the signal processing device 6 according to the first embodiment is configured to append the color gamut identification information to the ancillary data multiplex enabled region of the SDI data streams, by using the UID defined by the predetermined SDI format (by using the sections of use that are usable for the user in the data identification words (DID, SDID)). Further, the signal processing device 6 appends the color gamut identification information only to the Y data sequence, from between the Y data sequence and the $C_B/C_R$ data sequence in the SDI data streams.

Accordingly, it is possible to append the color gamut identification information, by simply defining in the data identification word (the DID) and the secondary data identification word (the SDID) structuring the UID that this UID serves as the color gamut identification information used for identifying the color gamut and further setting the user data word (UDW) with the value defining the calculation formula used in the matrix calculating process performed in the YC conversion. Consequently, it is also possible to keep the processing load of the signal processing device 6 small, even when using the configuration where the color gamut identification information is appended.

Second Embodiment

Next, a second embodiment of the present invention will be explained.

In the following sections, some of the configuration elements that are the same as those in the first embodiment above will be referred to by using the same reference characters, and detailed explanations thereof will be either omitted or simplified.

The medical observation system 1 according to the first embodiment described above uses, as a medical observation device of the present invention, the endoscope (a rigid endoscope) employing a rigid scope (the insertion part 21).

In contrast, a medical observation system according to the second embodiment uses, as a medical observation device of the present invention, a flexible endoscope employing a flexible scope.

A configuration of the medical observation system according to the second embodiment will be explained below.

Figure 7:
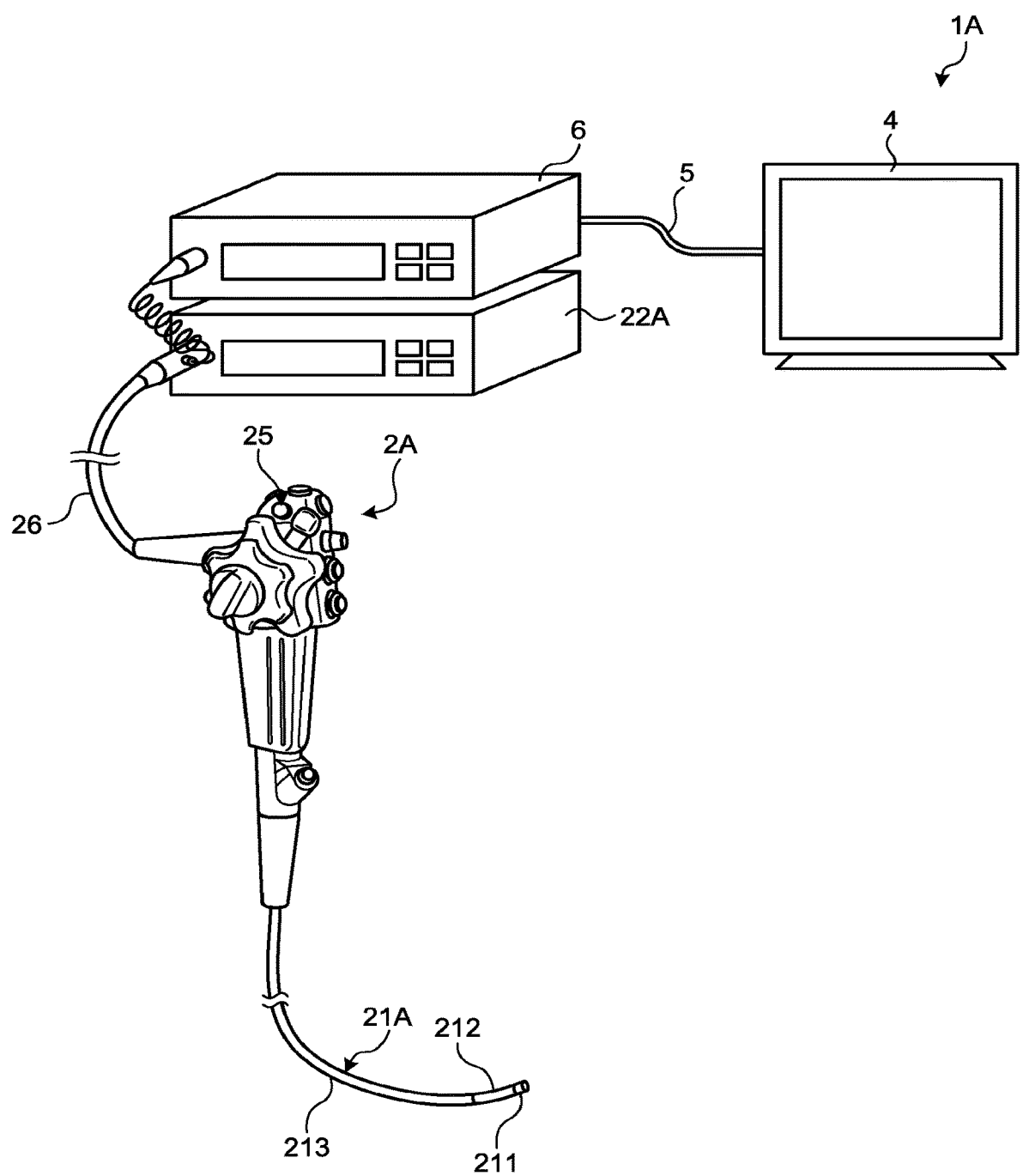
FIG. 7 is a drawing illustrating a schematic configuration of a medical observation system according to a second embodiment of the present invention.

FIG. 7 is a drawing illustrating a schematic configuration of a medical observation system 1A according to the second embodiment of the present invention.

As illustrated in FIG. 7, the medical observation system 1A according to the second embodiment includes: an endoscope 2A configured to generate an imaged signal (a raw signal) by taking an image of the inside of a body at an observation site, by inserting an insertion part 21A into the inside of the living body; a light source device 22A configured to generate illumination light to be emitted from the tip end of the endoscope 2A; the signal processing device 6 configured to receive an input of the raw signal generated by the endoscope 2A and to process the raw signal; and the display device 4 connected to the signal processing device 6 via the second transfer cable 5 and configured to display an image based on the picture signal processed by the signal processing device 6.

The endoscope 2A has functions as a medical observation device of the present invention. As illustrated in FIG. 7, the endoscope 2A has the insertion part 21A that has an oblong shape and is flexible; an operation part 25 that is connected to the basal end side of the insertion part 21A and is configured to receive inputs of various types of operation signals; and a universal cord 26 that extends from the operation part 25 in a direction different from the extending direction of the insertion part 21A and has built therein various types of cables connected to the light source device 22A and to the signal processing device 6. As illustrated in FIG. 7, the insertion part 21A includes a tip end part 211 that has built therein an imaging part (not illustrated) configured to image the inside of the living body and to generate the raw signal; a curved part 212 that is curvable and is configured with a plurality of curve pieces; and a flexible tube part 213 that is connected to the basal end side of the curved part 212 and is long and flexible. In the present example, the universal cord 26 has substantially the same configuration as that of the first transfer cable 3 described in the first embodiment above. Further, the signal processing device 6 and the display device 4 each perform the same processes as those in the first embodiment above, on the raw signal input thereto from the endoscope 2A via the universal cord 26.

Even when the flexible endoscope (the endoscope 2A) is used as described in the second embodiment above, it is possible to achieve the same advantageous effects as those achieved in the first embodiment above.

Third Embodiment

Next, a third embodiment of the present invention will be explained.

In the following sections, some of the configuration elements that are the same as those in the first embodiment above will be referred to by using the same reference characters, and detailed explanations thereof will be either omitted or simplified.

In the medical observation system 1 according to the first embodiment described above uses, as a medical observation device of the present invention, the endoscope (the rigid endoscope) employing the rigid scope (the insertion part 21).

In contrast, a medical observation system according to the third embodiment uses, as a medical observation device of the present invention, a surgical microscope configured to image a predetermined field-of-vision region in an enlarged manner.

A configuration of the medical observation system according to the third embodiment will be explained below.

Figure 8:
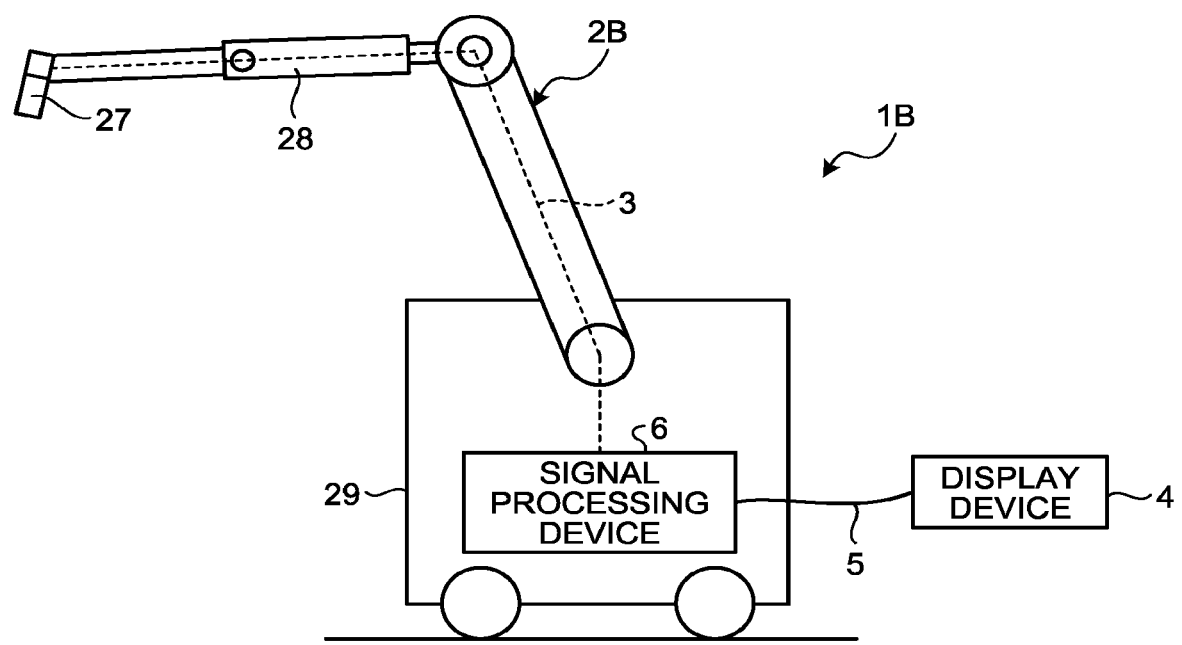
FIG. 8 is a diagram illustrating a schematic configuration of a medical observation system according to a third embodiment of the present invention.

FIG. 8 is a diagram illustrating a schematic configuration of a medical observation system 1B according to the third embodiment of the present invention.

As illustrated in FIG. 8, the medical observation system 1B according to the third embodiment includes: a surgical microscope 2B configured to take an image used for observing an imaged subject and to generate an imaged signal (a raw signal); the signal processing device 6 configured to receive an input of the raw signal generated by the surgical microscope 2B and to process the raw signal; and the display device 4 connected to the signal processing device 6 via the second transfer cable 5 and configured to display an image based on the picture signal processed by the signal processing device 6.

The surgical microscope 2B has functions as a medical observation device of the present invention. As illustrated in FIG. 8, the surgical microscope 2B includes: a microscope part 27 configured to image a minute site of the imaged subject in an enlarged manner and to generate the raw signal; a supporting part 28 that is connected to a basal end part of the microscope part 27 and includes an arm configured to rotatably support the microscope part 27; and a base part 29 that is configured to rotatably hold a basal end part of the supporting part 28 and is movable on a floor surface.

Further, as illustrated in FIG. 8, the signal processing device 6 is installed in the base part 29.

Alternatively, instead of being movable on a floor surface, the base part 29 may be configured to support the supporting part 28 while being fixed onto a ceiling, a wall surface, or the like. Further, the base part 29 may include a light source part configured to generate illumination light to be radiated onto the imaged subject from the surgical microscope 2B.

For example, the microscope part 27 has a circular cylindrical shape and has built therein an imaging part (not illustrated) configured to image the inside of the living body and to generate the raw signal. In the third embodiment, the microscope part 27 includes only one imaging part. Further, the raw signal generated by the imaging part is output to the signal processing device 6 via the first transfer cable 3 wired along the supporting part 28.

Provided on a lateral face of the microscope part 27 is a switch (not illustrated) configured to receive an input of an operation instruction for the surgical microscope 2B. Further, provided over an opening face in a lower end part of the microscope part 27 is cover glass (not illustrated) for protecting the interior.

The user such as an operator moves the microscope part 27 and performs a zooming operation, by operating any of various types of switches while holding the microscope part 27. It is desirable to configure the microscope part 27 to have an oblong shape extending in the observation direction to make it easy for the user to grasp the microscope part 27 and change the field-of-vision direction. Accordingly, the microscope part 27 may have a shape other than the circular cylindrical shape and may have a polygonal columnar shape, for example.

Further, the signal processing device 6 and the display device 4 each perform the same processes as those in the first embodiment above, on the raw signal input thereto from the surgical microscope 2B (the microscope part 27) via the first transfer cable 3.

Even when the surgical microscope 2B is used as described in the third embodiment above, it is possible to achieve the same advantageous effects as those achieved in the first embodiment above.

Fourth Embodiment

Next, a fourth embodiment of the present invention will be explained.

In the following sections, some of the configuration elements that are the same as those in the third embodiment above will be referred to by using the same reference characters, and detailed explanations thereof will be either omitted or simplified.

In the medical observation system 1B according to the third embodiment above, the microscope part 27 includes only one imaging part. In other words, the medical observation system 1B displays a view of the inside of the examined subject such as a human being (the inside of the living body) as a two-dimensional (2D) image.

In contrast, in a medical observation system according to the fourth embodiment, it is possible to display the inside of a living body as a three-dimensional (3D) image. Further, in the medical observation system according to the fourth embodiment, the information appended to a picture signal (a 3D picture signal in the fourth embodiment) output to a display device is different from that in the medical observation system 1B described in the third embodiment above.

In the following sections, configurations of a microscope part, a signal processing device, and a display device structuring the medical observation system according to the fourth embodiment will be explained.

A Configuration of a Microscope Part

Figure 9:
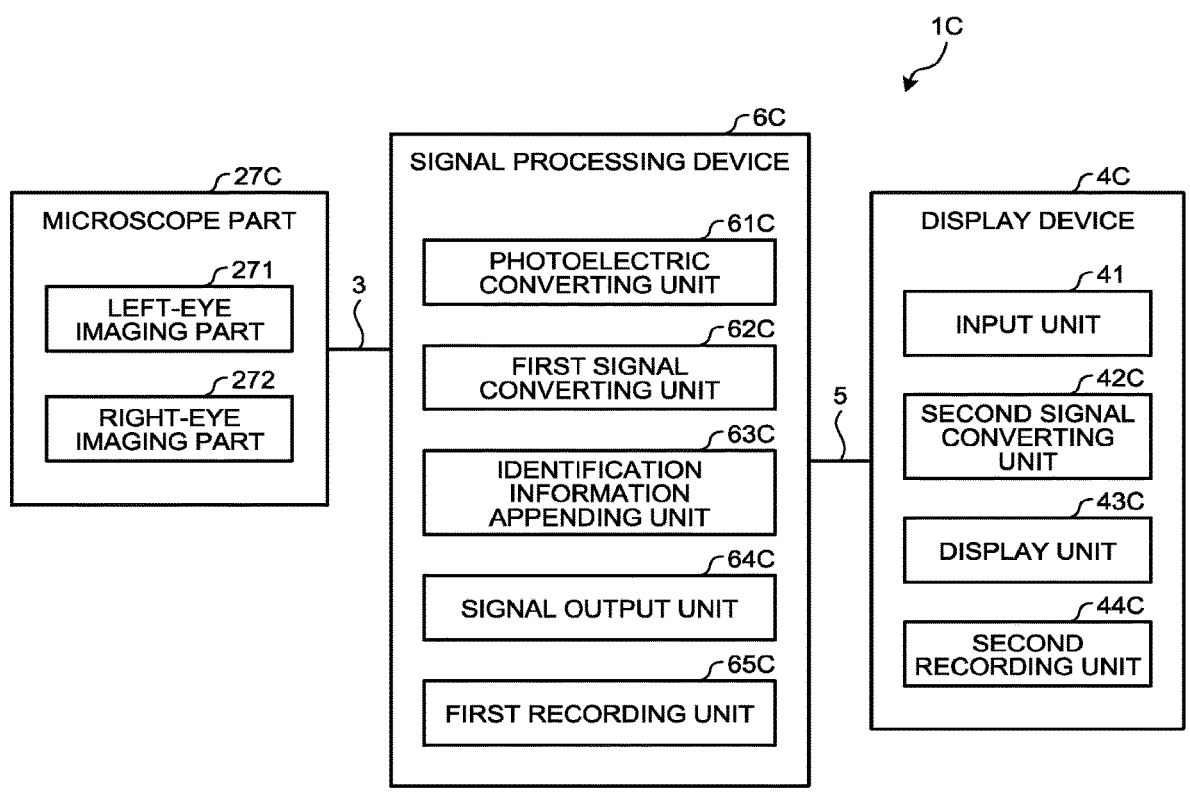
FIG. 9 is a block diagram illustrating configurations of a microscope part, a signal processing device, and a display device structuring a medical observation system according to a fourth embodiment of the present invention.

FIG. 9 is a block diagram illustrating configurations of a microscope part 27C, a signal processing device 6C, and a display device 4C structuring a medical observation system 1C according to the fourth embodiment of the present invention.

As illustrated in FIG. 9, the microscope part 27C includes two imaging parts, namely, a left-eye imaging part 271 and a right-eye imaging part 272 configure to take a left-eye image and a right-eye image, respectively, that have parallax with respect to each other.

Under control of the signal processing device 6C, the left-eye imaging part 271 is configured to take the left-eye image to be visually recognized by the left eye of the user such as a medical doctor who uses the medical observation system 1C and to generate a left-eye picture signal.

Under control of the signal processing device 6C, the right-eye imaging part 272 is configured to take the right-eye image to be visually recognized by the right eye of the user such as the medical doctor who uses the medical observation system 1C and to generate a right-eye picture signal.

In the fourth embodiment, the left-eye and the right-eye picture signals are each a 4K picture signal.

Further, the microscope part 27C performs a photoelectric conversion to convert each of the left-eye and the right-eye picture signals into an optical signal and further outputs the left-eye and the right-eye picture signals (the optical signals) resulting from the photoelectric conversion to the signal processing device 6C via the first transfer cable 3.

A Configuration of the Signal Processing Device

Next, a configuration of the signal processing device 6C will be explained, with reference to FIG. 9.

The signal processing device 6C has functions as a medical signal processing device of the present invention. As illustrated in FIG. 9, the signal processing device 6C includes a photoelectric converting unit 61C, a first signal converting unit 62C, an identification information appending unit 63C, a signal output unit 64C, and a first recording unit 65C.

The photoelectric converting unit 61C has functions as a signal input unit of the present invention and is configured to receive an input of each of the left-eye and the right-eye picture signals (the optical signals) from the microscope part 27C via the first transfer cable 3. Further, the photoelectric converting unit 61C performs a photoelectric conversion to convert each of the left-eye and the right-eye picture signals (the optical signals) into an electrical signal.

Figure 10A:
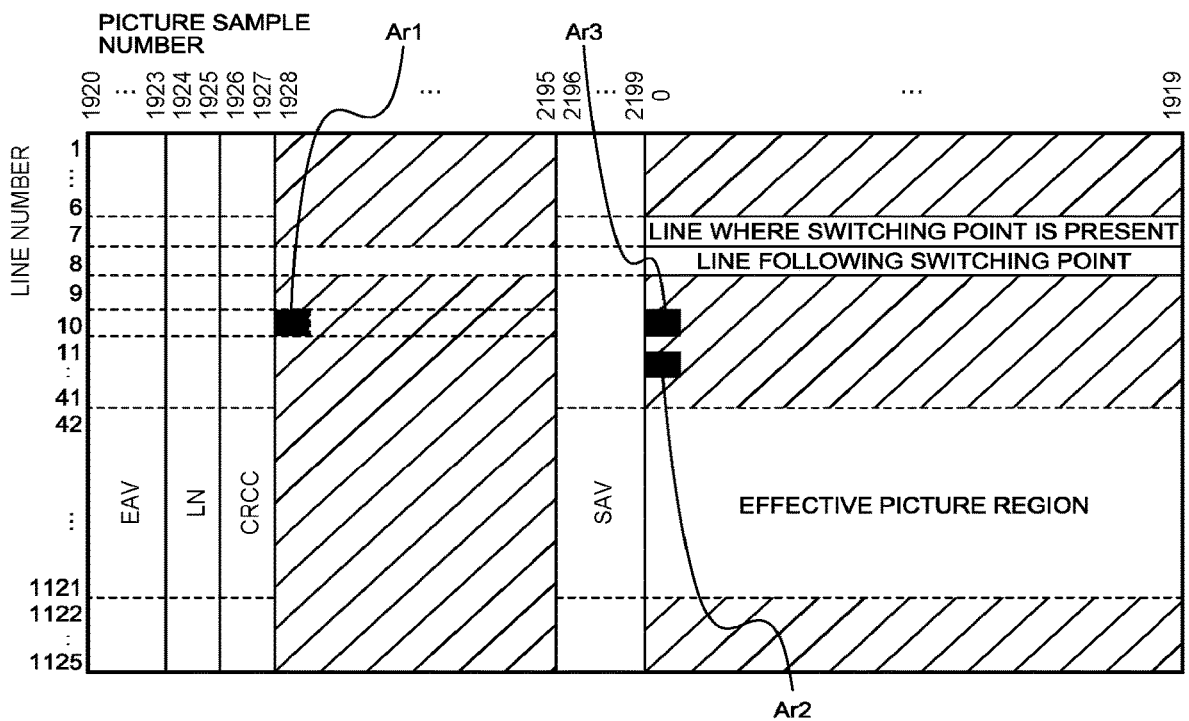
FIG. 10A is a drawing illustrating an example of an SDI data stream (a Y data sequence) resulting from a conversion performed by the first signal converting unit illustrated in FIG. 9.
Figure 10B:
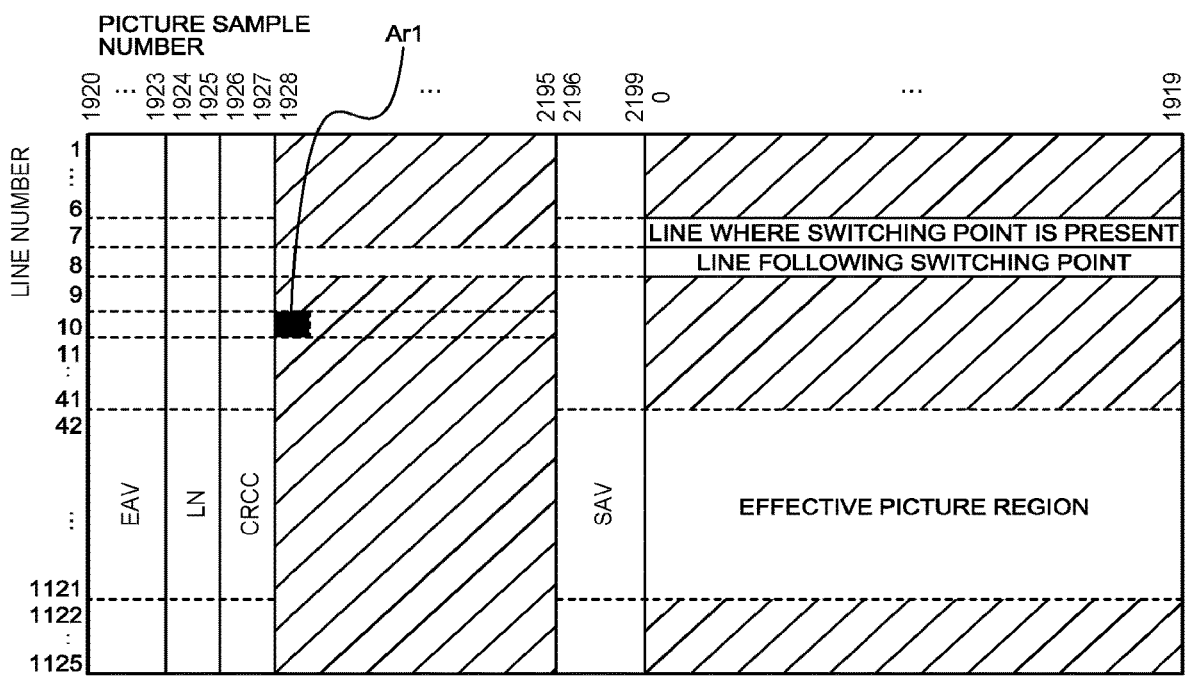
FIG. 10B is a drawing illustrating an example of another SDI data stream (a $C_B/C_R$ data sequence) resulting from the conversion performed by the first signal converting unit illustrated in FIG. 9.

FIG. 10A is a drawing illustrating an example of an SDI data stream (a Y data sequence) resulting from a conversion performed by the first signal converting unit 62C. FIG. 10B is a drawing illustrating an example of another SDI data stream (a $C_B/C_R$ data sequence) resulting from the conversion performed by the first signal converting unit 62C.

The first signal converting unit 62C is configured to perform the YC conversion explained in the first embodiment above on the left-eye and the right-eye picture signals resulting from the photoelectric conversion performed by the photoelectric converting unit 61C.

Further, the first signal converting unit 62C is configured to generate a 3D picture signal (a Y, $C_B/C_R$ signal) compliant with a Line by Line scheme (a 3D transfer scheme) from the left-eye and the right-eye picture signals (the Y, $C_B/C_R$ signals) resulting from the YC conversion, by using a publicly-known method. In the fourth embodiment, the 3D picture signal is a 4K picture signal.

Further, similarly to the first embodiment explained above, the first signal converting unit 62C is configured to convert the 3D picture signal (the Y, $C_B/C_R$ signal) into SDI data streams (a Y data sequence and a $C_B/C_R$ data sequence) corresponding to multiple channels (e.g., four channels) defined by a format of a predetermined SDI scheme (e.g., 3G-SDI, Level A) (FIGS. 10A and 10B).

Similarly to the first embodiment described above, to the SDI data streams resulting from the conversion performed by the first signal converting unit 62C, the identification information appending unit 63C is configured to append the color gamut identification information and to also append scheme identification information related to the 3D transfer scheme (the line by line scheme). In the fourth embodiment, the identification information appending unit 63C uses, as the scheme identification information, "a 3D Frame Compatible (3DFC) ancillary data packet" defined by SMPTE ST 2068. From between the Y data sequence and the CB/CR data sequence in the SDI data streams, the identification information appending unit 63C appends the scheme identification information (the 3DFC ancillary data packet) only to the Y data sequence. In the vertical ancillary data region (VANC) of the SDI data stream (the Y data sequence), the identification information appending unit 63C appends the scheme identification information (the 3DFC ancillary data packet) to the region (indicated with solid black as a third region Ar3 in 10A) corresponding to picture sample numbers "0" to "9" in line number "10". Further, the identification information appending unit 63C appends the scheme identification information (the 3DFC ancillary data packet) to the SDI data stream (only the Y data sequence) corresponding to all the channels (e.g., the four channels) resulting from the conversion performed by the first signal converting unit 62C.

In this situation, the 3DFC ancillary data packet is a packet defined by SMPTE ST 2068 as information identifying any of three frame packing schemes, namely, a Side by Side scheme, a Top and Bottom scheme, and a Temporal Interleave scheme. In other words, when the 3DFC ancillary data packet is simply used, it is not possible to identify the Line by Line scheme used in the fourth embodiment. Further, similarly to the color gamut identification information (the UID), the 3DFC ancillary data packet is structured with an ancillary data flag (ADF), a data identification word (DID), a secondary data identification word (SDID), a data count word (DC), a user data word (UDW), and a checksum word (CS). Further, among these, the user data word (UDW) is structured with a payload identifying any of the above-mentioned three frame packing schemes.

FIG. 11 is a table illustrating payloads defined by SMPTE ST 2068.

As illustrated in FIG. 11, the user data word (UDW) is configured with three words each of which has 10 bits.

Further, of the user data word (UDW) configured with the three words, the "Frame Packed Signal (FPS)" in the bit position b2 of UDW1 indicates whether or not the picture signal is a 3D picture signal. More specifically, when having the value "0", the "FPS" indicates that the picture signal is not a 3D picture signal. On the contrary, when having the value "1", the "FPS" indicates that the picture signal is a 3D picture signal. Accordingly, the identification information appending unit 63C sets the "FPS" to the value "1".

Further, the pieces of information "frame packing arrangement (fpa) 3" to "fpa 0" in the bit positions b7 to b4 of UDW1 indicate a frame packing scheme. More specifically, when having the value "0011", "fpa3" to "fpa0" indicate that the frame packing scheme is the Side by Side scheme. In another example, when having the value "0100", "fpa3" to "fpa0" indicate that the frame packing scheme is the Top and Bottom scheme. In yet another example, when having the value "0101", "fpa3" to "fpa0" indicate that the frame packing scheme is the Temporal Interleave scheme. In yet another example, when having the value "0000", "fpa3" to "fpa0" indicate that the scheme is undefined (reserved).

Further, to indicate that the 3D transfer scheme is the Line by Line scheme, the identification information appending unit 63C sets "fpa3" to "fpa0" to the value "0000" by using the undefined sections of use.

Via the second transfer cable 5, the signal output unit 64C is configured to output the SDI data streams (the Y data sequence and the $C_B/C_R$ data sequence) corresponding to the multiple channels (e.g., the four channels) and having the color gamut identification information (the UID) and the scheme identification information (the 3DFC ancillary data packet) appended thereto, to the display device 4C.

The first recording unit 65C is configured to record therein data and the like required by various types of processes performed by the first signal converting unit 62C and the identification information appending unit 63C.

A Configuration of the Display Device

Next, a configuration of the display device 4C will be explained, with reference to FIG. 9.

The display device 4C has functions as a medical display device of the present invention. As illustrated in FIG. 9, the display device 4C includes a second signal converting unit 42C, a display unit 43C, and a second recording unit 44C, in addition to the input unit 41 explained in the third embodiment above.

The second signal converting unit 42C is configured to receive an input of the SDI data streams (the Y data sequence and the $C_B/C_R$ data sequence) corresponding to multiple channels (e.g., four channels) from the signal processing device 6C via the second transfer cable 5 and the input unit 41. After that, similarly to the first embodiment described above, the second signal converting unit 42C is configured to convert the SDI data streams into the 3D picture signal (the Y, $C_D/C_R$ signal) observed prior to the conversion into the SDI data streams and to also perform an RGB conversion on the 3D picture signal (the Y, $C_B/C_R$ signal) resulting from the conversion.

Further, in the scheme identification information (the 3DFC ancillary data packet) appended to the third region Ar3 (FIG. 10A) in the vertical ancillary data region (VANC) of the SDI data streams, because the value of the "FPS" in the bit position B2 of UDW1 is "0", the second signal converting unit 42C learns that a 3D picture signal was output from the signal processing device 6C. Further, the second signal converting unit 42C learns that the 3D transfer scheme of the 3D picture signal is the Line by Line scheme, because the value of "fpa3" to "fpa0" in the bit positions b7 to b4 of UDW1 is the value "0000" denoting undefined (reserved). Further, the second signal converting unit 42C generates a display-purpose 3D picture signal (an RGB signal) by performing a signal processing process (e.g., a parallax adjustment, or the like) corresponding to the Line by Line scheme, on the 3D picture signal (the RGB signal) resulting from the RGB conversion.

The display unit 43C is configured with a 3D display device capable of realizing 3D display by using the Line by Line scheme. Further, the display unit 43C is configured to display a 3D image based on the display-purpose 3D picture signal (the RGB signal) generated by the second signal converting unit 42C. The user such as a medical doctor who uses the medical observation system 1C stereoscopically views the 3D image by visually recognizing, on his/her left eye and right eye, the 3D image displayed by the display unit 43C, via polarized glasses (not illustrated). The second recording unit 44C is configured to record therein data and the like that are required by various types of processes performed by the second signal converting unit 42C.

Even when the medical observation system 1C capable of realizing the 3D display is used as described in the fourth embodiment above, it is possible to achieve the same advantageous effects as those achieved in the first embodiment.

In the fourth embodiment, the signal processing device 6C is configured to output the 3D picture signal to the display device 4C by using the Line by Line scheme. As a characteristic of the 3D picture signal using the Line by Line scheme, the picture signal may also be displayed as a 2D image on the display device 4C side. Accordingly, for processing the 3D picture signal, the same circuit path as one for a 2D picture signal can be used. In other words, in the display device 4C, it is possible to keep small the delay amount in displaying the 3D image. In particular, in medical fields, because medical manipulations are performed while the operator is looking at 3D images displayed in a real-time manner, it is effective to keep the delay amount small.

Further, as explained above, according to SMPTE ST 2068, no information to identify the Line by Line scheme is defined in the 3DFC ancillary data packet. For this reason, even if a 3DFC ancillary data packet were simply appended by the signal processing device for the display device, and the 3D picture signal is output by using the Line by Line scheme, it would be impossible to recognize the 3D transfer scheme (the Line by Line scheme) of the 3D picture signal on the display device side. In other words, it would be impossible, on the display device side, to perform a signal processing process corresponding to the Line by Line scheme on the 3D picture signal. It would therefore be impossible to enable the user such as a medical doctor to have a stereoscopic view properly.

In contrast, according to the fourth embodiment, the arrangement is made between the signal processing device 6C and the display device 4C so that when the value in the bit positions b7 to b4 of UDW1 in the 3DFC ancillary data packet is the value "0000" denoting undefined, it means that the Line by Line scheme is used. Accordingly, there is no need to use information other than the 3DFC ancillary data packet for the purpose of making it possible, on the display device 4C side, to recognize the 3D transfer scheme (the Line by Line scheme) of the 3D picture signal. It is therefore possible to make the design more efficient. Further, on the display device 4C side, because it is possible to perform the signal processing process corresponding to the Line by Line scheme on the 3D picture signal, it is possible to enable the user such as a medical doctor to have a stereoscopic view properly.

Other Embodiments

Some embodiments to carry out the present invention have thus been explained. However, the present invention is not limited only to the first to the fourth embodiments described above.

In the first to the fourth embodiments described above, as medical observation devices of the present invention, the endoscope 2 (the rigid endoscope) using the rigid scope (the insertion part 21), the endoscope 2A (the flexible endoscope) using the flexible scope (not illustrated), and the surgical microscope 2B are used. However, possible embodiments are not limited to these examples. It is acceptable to use other medical observation devices such as ultrasound endoscopes or the like.

In the first to the fourth embodiments described above, as the medical observation systems 1 and 1A to 1C, it is also acceptable to use a configuration in which a recorder (corresponding to a medical recording device of the present invention) is connected to the signal processing device 6 or 6C and to the display device 4 or 4C, via a transfer cable compliant with a transfer standard of a predetermined SDI scheme (e.g., HD-SDI, 3G-SDI, or the like).

It is desirable to configure the recorder so that, when recording therein the picture signal (the SDI data streams corresponding to multiple channels) output from the signal processing device 6 or 6C and outputting the recorded picture signal to the display device 4 or 4C, the recorder outputs the color gamut identification information and the scheme identification information together therewith, like the picture signal output from the signal processing device 6 or 6C to the display device 4 or 4C.

In the first to the fourth embodiments described above, the display device 4 or 4C performs the RGB conversion so as to realize the same color gamut as the color gamut of the picture signal processed by the signal processing device 6 or 6C. However, possible embodiments are not limited to this example. For instance, another arrangement is acceptable in which the color gamut identification information related to the color gamut of the picture signal processed by the signal processing device 6 or 6C is learned so that, based on the color gamut identification information, an RGB conversion is performed so as to realize a color gamut different from the color gamut of the picture signal processed by the signal processing device 6 or 6C.

Further, in the first to the fourth embodiments described above, the examples are explained in which the raw signal or the left-eye and the right-eye picture signals output from the camera head 24, the endoscope 2A, or the surgical microscope 2B are each a 4K picture signal; however, possible embodiments are not limited to these examples. The present invention is also applicable to situations where other types of picture signals are output such as a Standard Definition (SD) picture signal, a High Definition (HD) picture signal, or a picture signal of 8K or larger.

Further, the flow of the process is not limited by the processing orders illustrated in the flowcharts (FIGS. 5 and 6) explained in the first to the fourth embodiments above. It is acceptable to modify the processing flows as long as no conflict occurs.

Further, it is possible to write, as a computer program (hereinafter, "program"), an algorithm of any of the processes explained in the present disclosure with reference to the flowcharts. Such a program may be recorded in a recording unit (e.g., the first recording unit 65, 65C or a second recording unit 44, 44C) provided within a computer or may be recorded on a computer-readable recording medium. The program may be recorded into the recording unit or onto the recording medium, when the computer or the recording medium is shipped as a product or as being downloaded via a communication network.

In the fourth embodiment described above, the 3DFC ancillary data packet defined by SMPTE ST 2068 is used as the scheme identification information; however, possible embodiments are not limited to this example. For instance, similarly to the color gamut identification information (the UID), it is also acceptable to use a UID defined by a predetermined SDI format as the scheme identification information.

REFERENCE SIGNS LIST 1, 1A to 1C MEDICAL OBSERVATION SYSTEM
2, 2A ENDOSCOPE
2B SURGICAL MICROSCOPE
3 FIRST TRANSFER CABLE
4, 4C DISPLAY DEVICE
5 SECOND TRANSFER CABLE
6, 6C SIGNAL PROCESSING DEVICE
7 THIRD TRANSFER CABLE
21, 21A INSERTION PART
22, 22A LIGHT SOURCE DEVICE
23 LIGHT GUIDE
24 CAMERA HEAD
25 OPERATION PART
26 UNIVERSAL CORD
27, 27C MICROSCOPE PART
28 SUPPORTING PART
29 BASE PART
41 INPUT UNIT
42, 42C SECOND SIGNAL CONVERTING UNIT
43, 43C DISPLAY UNIT
44, 44C SECOND RECORDING UNIT
61, 61C PHOTOELECTRIC CONVERTING UNIT
62, 62C FIRST SIGNAL CONVERTING UNIT
63, 63C IDENTIFICATION INFORMATION APPENDING UNIT
64, 64C SIGNAL OUTPUT UNIT
65, 65C FIRST RECORDING UNIT
211 TIP END PART
212 CURVED PART
213 FLEXIBLE TUBE PART
271, 272 LEFT-, RIGHT-EYE IMAGING PART
Ar1 to Ar3 FIRST TO THIRD REGIONS

The invention claimed is:

1. A medical signal processing device that receives a picture signal imaged by a medical observation device and processes the picture signal, comprising:
a signal input circuit that receives the picture signal;
a first signal converting circuit that converts the picture signal received by the signal input circuit from an RGB signal into a luminance signal and a color difference signal by performing a matrix calculating process;
an identification information appending circuit that appends color gamut identification information related to a color gamut of the picture signal and corresponding to the matrix calculating process, to the picture signal resulting from the conversion; and
a signal output circuit that outputs the picture signal to which the color gamut identification information has been appended, to either an external medical display device or an external medical recording device,
wherein the signal input circuit receives two picture signals including a left-eye picture signal and a right-eye picture signal,
the first signal converting circuit converts the left-eye picture signal and the right-eye picture signal received by the signal input circuit each from the RGB signal into the luminance signal and the color difference signal by performing the matrix calculating process and generates a 3D picture signal from the left-eye picture signal and the right-eye picture signal resulting from the conversion,
to the 3D picture signal, the identification information appending circuit appends the color gamut identification information and appends scheme information identifying a 3D transfer scheme that generates the 3D picture signal from the left-eye picture signal and the right-eye picture signal, and the signal output circuit outputs the 3D picture signal to which the color gamut identification information and the scheme identification information have been appended, to either the medical display device or the medical recording device, wherein the scheme information identifying a 3D transfer scheme includes an identifier, a first value of the identifier indicating a line by line scheme and a second value of the identifier indicating a 3D transfer scheme different from the line by line scheme.

2. The medical signal processing device according to claim 1, wherein the picture signal imaged by the medical observation device is a picture signal having a 4K resolution level.

3. The medical signal processing device according to claim 1, wherein the first signal converting circuit converts the picture signal received by the signal input circuit from the RGB signal into the luminance signal and the color difference signal by performing the matrix calculating process and converts the picture signal resulting from the conversion into serial data defined by a predetermined SDI format, and the identification information appending circuit appends the color gamut identification information by using a section of use that is usable by a user and is in a data identification word defined by the predetermined SDI format.

4. The medical signal processing device according to claim 1, wherein the first signal converting circuit converts the picture signal received by the signal input circuit from the RGB signal into the luminance signal and the color difference signal by performing the matrix calculating process and converts the picture signal resulting from the conversion into serial data defined by a predetermined SDI format, and the identification information appending circuit appends the color gamut identification information to an ancillary data multiplex enabled region that is in the serial data and is defined by the predetermined SDI format.

5. The medical signal processing device according to claim 1, wherein the first signal converting circuit converts the picture signal received by the signal input circuit from the RGB signal into the luminance signal and the color difference signal by performing the matrix calculating process and also converts the picture signal resulting from the conversion into serial data defined by a predetermined SDI format, and the identification information appending circuit appends the color gamut identification information only to a Y data sequence from between the Y data sequence and a CB/CR data sequence in the serial data.

6. The medical signal processing device according to claim 1, wherein the 3D transfer scheme is a line by line scheme.

7. The medical signal processing device according to claim 1, wherein the identification information appending circuit uses a 3DFC ancillary data packet defined by SMPTE ST 2068 as the scheme identification information.

8. The medical signal processing device according to claim 7, wherein the identification information appending circuit uses an undefined section of use of a payload in the 3DFC ancillary data packet, as the scheme identification information.

9. The medical signal processing device according to claim 2, wherein the first signal converting circuit converts the picture signal received by the signal input circuit by performing either the matrix calculating process compliant with ITU-R BT.709 or the matrix calculating process compliant with ITU-R BT.2020, when the first signal converting circuit performed the conversion by performing the matrix calculating process compliant with ITU-R BT.709, the identification information appending circuit appends the color gamut identification information indicating ITU-R BT.709 to the picture signal resulting from the conversion, and when the first signal converting circuit performed the conversion by performing the matrix calculating process compliant with ITU-R BT.2020, the identification information appending circuit appends the color gamut identification information indicating ITU-R BT.2020 to the picture signal resulting from the conversion.

10. A medical display device that receives a picture signal processed by an external medical signal processing device and displays an image based on the picture signal, wherein the picture signal has appended thereto color gamut identification information related to a color gamut of the picture signal and corresponding to a matrix calculating process performed when the medical signal processing device converted the picture signal from an RGB signal into a luminance signal and a color difference signal, and the medical display device comprises:

a second signal converting circuit that generates a display-purpose picture signal by converting the picture signal from the luminance signal and the color difference signal into the RGB signal in accordance with the matrix calculating process, based on the color gamut identification information appended to the picture signal; and a display that displays an image based on the display-purpose picture signals, wherein the color gamut identification information appended to the picture signal includes information indicating ITU-R BT.709 or indicating ITU-R BT.2020, wherein the picture signal is a 3-D picture signal including a left-eye picture signal and a right-eye picture signal, wherein the 3D picture signal has appended thereto scheme information identifying a 3D transfer scheme that generated the 3D picture signal from the left-eye picture signal and the right-eye picture signal, wherein the scheme information identifying a 3D transfer scheme includes an identifier, a first value of the identifier indicating a line by line scheme and a second value of the identifier indicating a 3D transfer scheme different from the line by line scheme.

11. The medical display device according to claim 10, wherein the second signal converting circuit generates the display-purpose picture signal, by converting the 3D picture signal from the luminance signal and the color difference signal into the RGB signal in accordance with the matrix calculating process, based on the color gamut identification information appended to the 3D picture signal, and performing a signal processing process corresponding to the 3D transfer scheme of the 3D picture signal, based on the scheme identification information appended to the 3D picture signal.

12. A medical observation system comprising:
a medical observation device that images an inside of an examined subject and supplies a picture signal obtained by the imaging;
a medical signal processing device that receives the picture signal and processes the picture signal; and
a medical display device that displays an image based on the picture signal processed by the medical signal processing device, wherein
the medical signal processing device includes:
  a signal input circuit that receives the picture signal;
  a first signal converting circuit that converts the picture signal received by the signal input circuit from an RGB signal into a luminance signal and a color difference signal by performing a matrix calculating process;
  an identification information appending circuit that appends color gamut identification information related to a color gamut of the picture signal and corresponding to the matrix calculating process, to the picture signal resulting from the conversion; and
  a signal output circuit that outputs the picture signal to which the color gamut identification information has been appended, to the medical display device, and
the medical display device includes:
  a second signal converting circuit that generates a display-purpose picture signal by converting the picture signal from the luminance signal and the color difference signal into the RGB signal in accordance with the matrix calculating process, based on the color gamut identification information appended to the picture signal; and
  a display that displays an image based on the display-purpose picture signals,
wherein the signal input circuit receives two picture signals including a left-eye picture signal and a right-eye picture signal,
the first signal converting circuit converts the left-eye picture signal and the right-eye picture signal received by the signal input circuit each from the RGB signal into the luminance signal and the color difference signal by performing the matrix calculating process and generates a 3D picture signal from the left-eye picture signal and the right-eye picture signal resulting from the conversion,
to the 3D picture signal, the identification information appending circuit appends the color gamut identification information and appends scheme information identifying a 3D transfer scheme that generates the 3D picture signal from the left-eye picture signal and the right-eye picture signal, and
the signal output circuit outputs the 3D picture signal to which the color gamut identification information and the scheme identification information have been appended, to either the medical display device or the medical recording device,
wherein the scheme information identifying a 3D transfer scheme includes an identifier, a first value of the identifier indicating a line by line scheme and a second value of the identifier indicating a 3D transfer scheme different from the line by line scheme.

13. The medical observation system according to claim 12, wherein the medical observation device is an endoscope.

14. The medical observation system according to claim 12, wherein the first signal converting circuit converts the picture signal received by the signal input circuit by performing either the matrix calculating process compliant with ITU-R BT.709 or the matrix calculating process compliant with ITU-R BT.2020,
when the first signal converting circuit performed the conversion by performing the matrix calculating process compliant with ITU-R BT.709, the identification information appending circuit appends the color gamut identification information indicating ITU-R BT.709 to the picture signal resulting from the conversion, and
when the first signal converting circuit performed the conversion by performing the matrix calculating process compliant with ITU-R BT.2020, the identification information appending circuit appends the color gamut identification information indicating ITU-R BT.2020 to the picture signal resulting from the conversion.

\* \* \* \* \*